(12) United States Patent
Mourich et al.

(10) Patent No.: US 11,020,417 B2
(45) Date of Patent: Jun. 1, 2021

(54) METHODS AND COMPOUNDS FOR TREATMENT OF LYMPHOCYTE-RELATED DISEASES AND CONDITIONS

(71) Applicant: Sarepta Therapeutics, Inc., Cambridge, MA (US)

(72) Inventors: Dan V. Mourich, Salem, OR (US); Gunnar J. Hanson, Cambridge, MA (US); Frederick Joseph Schnell, Corvallis, OR (US); Johannes Christian Dworzak, Medford, MA (US)

(73) Assignee: Sarepta Therapeutics, Inc, Cambridge, MA (US)

( * ) Notice: Subject to any disclaimer, the term of this patent is extended or adjusted under 35 U.S.C. 154(b) by 0 days.

(21) Appl. No.: 15/579,497

(22) PCT Filed: Jun. 3, 2016

(86) PCT No.: PCT/US2016/035671
§ 371 (c)(1),
(2) Date: Dec. 4, 2017

(87) PCT Pub. No.: WO2016/196897
PCT Pub. Date: Dec. 8, 2016

(65) Prior Publication Data
US 2018/0161359 A1 Jun. 14, 2018

Related U.S. Application Data

(60) Provisional application No. 62/171,102, filed on Jun. 4, 2015.

(51) Int. Cl.
*C12N 15/113* (2010.01)
*A61K 31/7125* (2006.01)
*A61P 35/00* (2006.01)
*A61P 37/06* (2006.01)
*A61K 31/675* (2006.01)

(52) U.S. Cl.
CPC ........ *A61K 31/7125* (2013.01); *A61K 31/675* (2013.01); *A61P 35/00* (2018.01); *A61P 37/06* (2018.01); *C12N 15/113* (2013.01); *C12N 2310/11* (2013.01); *C12N 2310/3233* (2013.01)

(58) Field of Classification Search
CPC ........... A61K 31/7125; C12N 15/111; C12N 15/113; C12N 2310/11; C12N 2310/3233; C12N 2310/346
See application file for complete search history.

(56) References Cited

U.S. PATENT DOCUMENTS

| | | |
|---|---|---|
| 5,034,506 A | 7/1991 | Summerton et al. |
| 5,087,617 A | 2/1992 | Smith |
| 5,138,045 A | 8/1992 | Cook et al. |
| 5,142,047 A | 8/1992 | Summerton et al. |
| 5,166,315 A | 11/1992 | Summerton et al. |
| 5,185,444 A | 2/1993 | Summerton et al. |
| 5,212,295 A | 5/1993 | Cook |
| 5,217,866 A | 6/1993 | Summerton et al. |
| 5,218,105 A | 6/1993 | Cook et al. |
| 5,223,168 A | 6/1993 | Holt |
| 5,378,825 A | 1/1995 | Cook et al. |
| 5,386,023 A | 1/1995 | Sanghvi et al. |
| 5,457,191 A | 10/1995 | Cook et al. |
| 5,459,255 A | 10/1995 | Cook et al. |
| 5,479,847 A | 1/1996 | Powers et al. |
| 5,506,337 A | 4/1996 | Summerton et al. |
| 5,506,351 A | 4/1996 | McGee |
| 5,521,063 A | 5/1996 | Summerton et al. |
| 5,521,302 A | 5/1996 | Cook |

(Continued)

FOREIGN PATENT DOCUMENTS

| | | |
|---|---|---|
| EP | 0 892 064 A2 | 1/1999 |
| EP | 0 894 857 A2 | 2/1999 |

(Continued)

OTHER PUBLICATIONS

Hussell et al., Th1 and Th2 cytokine induction in pulmonary T cells during infection with respiratory syncytial virus, Journal of General Virology, vol. 77, pp. 2447-2455. (Year: 1996).*

(Continued)

*Primary Examiner* — Dana H Shin
(74) *Attorney, Agent, or Firm* — Lathrop GPM LLP; Brian C. Trinque

(57) ABSTRACT

Methods for treatment of lymphocyte-related diseases and conditions, such as cancer and autoimmune diseases, are provided. The methods comprise administration of an effective amount of an oligomer to a patient in need thereof, wherein the oligomer comprises, inter alia, at least one intersubunit linkage having the following structure: wherein $R^1$, $L^1$, X, Y and Z are as defined herein.

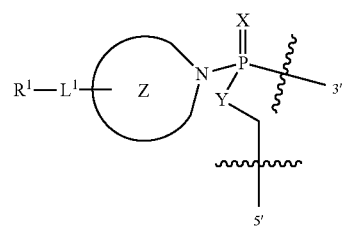

18 Claims, 5 Drawing Sheets
Specification includes a Sequence Listing.

(56) References Cited

U.S. PATENT DOCUMENTS

| | | |
|---|---|---|
| 5,525,465 A | 6/1996 | Haralambidis et al. |
| 5,539,082 A | 7/1996 | Nielsen et al. |
| 5,541,307 A | 7/1996 | Cook et al. |
| 5,554,746 A | 9/1996 | Ravikumar et al. |
| 5,571,902 A | 11/1996 | Ravikumar et al. |
| 5,576,302 A | 11/1996 | Cook et al. |
| 5,578,718 A | 11/1996 | Cook et al. |
| 5,580,767 A | 12/1996 | Cowsert et al. |
| 5,587,361 A | 12/1996 | Cook et al. |
| 5,587,469 A | 12/1996 | Cook et al. |
| 5,587,470 A | 12/1996 | Cook et al. |
| 5,599,797 A | 2/1997 | Cook et al. |
| 5,602,240 A | 2/1997 | De Mesmaeker et al. |
| 5,608,046 A | 3/1997 | Cook et al. |
| 5,610,289 A | 3/1997 | Cook et al. |
| 5,686,564 A | 11/1997 | Brundish et al. |
| 5,698,685 A | 12/1997 | Summerton et al. |
| 5,702,891 A | 12/1997 | Kolberg et al. |
| 5,734,039 A | 3/1998 | Calabretta et al. |
| 5,747,641 A | 5/1998 | Frankel et al. |
| 5,749,847 A | 5/1998 | Zewert et al. |
| 5,801,154 A | 9/1998 | Baracchini et al. |
| 5,821,052 A | 10/1998 | Chen et al. |
| 5,849,727 A | 12/1998 | Porter et al. |
| 5,892,023 A | 4/1999 | Pirotzky et al. |
| 5,955,318 A | 9/1999 | Simons et al. |
| 5,977,340 A | 11/1999 | Pirotzky et al. |
| 6,030,954 A | 2/2000 | Wu et al. |
| 6,060,456 A | 5/2000 | Arnold, Jr. et al. |
| 6,133,246 A | 10/2000 | McKay et al. |
| 6,159,946 A | 12/2000 | Zalewski et al. |
| 6,174,868 B1 | 1/2001 | Anderson et al. |
| 6,228,579 B1 | 5/2001 | Zyskind et al. |
| 6,239,265 B1 | 5/2001 | Cook |
| 6,245,747 B1 | 6/2001 | Porter et al. |
| 6,262,241 B1 | 7/2001 | Cook et al. |
| 6,303,573 B1 | 10/2001 | Rouslahti et al. |
| 6,306,993 B1 | 10/2001 | Rothbard et al. |
| 6,329,501 B1 | 12/2001 | Smith et al. |
| 6,365,351 B1 | 4/2002 | Iversen |
| 6,391,542 B1 | 5/2002 | Anderson et al. |
| 6,495,663 B1 | 12/2002 | Rothbard et al. |
| 6,548,651 B1 | 4/2003 | Nielsen et al. |
| 6,559,279 B1 | 5/2003 | Manoharan et al. |
| 6,593,292 B1 | 7/2003 | Rothbard et al. |
| 6,645,974 B2 | 11/2003 | Hutchinson et al. |
| 6,669,951 B2 | 12/2003 | Rothbard et al. |
| 6,677,153 B2 | 1/2004 | Iversen |
| 6,784,291 B2 | 8/2004 | Iversen et al. |
| 6,828,105 B2 | 12/2004 | Stein et al. |
| 6,841,542 B2 | 1/2005 | Bartelmez et al. |
| 7,049,431 B2 | 5/2006 | Iversen |
| 7,094,765 B1 | 8/2006 | Iversen et al. |
| 7,115,374 B2 | 10/2006 | Linnen |
| 7,138,238 B2 | 11/2006 | Vodyanoy et al. |
| 7,169,814 B2 | 1/2007 | Rothbard et al. |
| 7,402,574 B2 | 7/2008 | Iversen et al. |
| 7,456,146 B2 | 11/2008 | Yu et al. |
| 7,468,418 B2 | 12/2008 | Iversen et al. |
| 7,482,016 B2 | 1/2009 | Doerr et al. |
| 7,507,196 B2 | 3/2009 | Stein et al. |
| 7,524,829 B2 | 4/2009 | Stein et al. |
| 7,582,615 B2 | 9/2009 | Neuman et al. |
| 7,585,834 B2 | 9/2009 | Wender et al. |
| 7,625,873 B2 | 12/2009 | Geller et al. |
| 7,786,151 B2 | 8/2010 | Hagiwara et al. |
| 7,790,694 B2 | 9/2010 | Geller et al. |
| 7,807,801 B2 | 10/2010 | Iversen et al. |
| 7,838,657 B2 | 11/2010 | Singh et al. |
| 7,855,283 B2 | 12/2010 | Iversen |
| 7,888,012 B2 | 2/2011 | Iversen et al. |
| 7,943,762 B2 | 5/2011 | Weller et al. |
| 7,973,015 B2 | 7/2011 | van Ommen et al. |
| 7,989,608 B2 | 8/2011 | Mourich et al. |
| 8,008,469 B2 | 8/2011 | Mourich et al. |
| 8,030,291 B2 | 10/2011 | Stein et al. |
| 8,030,292 B2 | 10/2011 | Stein et al. |
| 8,053,420 B2 | 11/2011 | Iversen et al. |
| 8,067,569 B2 | 11/2011 | Iversen et al. |
| 8,067,571 B2 | 11/2011 | Weller et al. |
| 8,076,476 B2 | 12/2011 | Reeves et al. |
| 8,084,433 B2 | 12/2011 | Iversen et al. |
| 8,129,352 B2 | 3/2012 | Iversen et al. |
| 8,168,604 B2 | 5/2012 | Stein et al. |
| 8,198,429 B2 | 6/2012 | Iversen et al. |
| 8,299,206 B2 | 10/2012 | Fox et al. |
| 8,314,072 B2 | 11/2012 | Geller et al. |
| 8,329,668 B2 | 12/2012 | Stein et al. |
| 8,536,147 B2 | 9/2013 | Weller et al. |
| 8,741,863 B2 | 6/2014 | Moulton et al. |
| 8,779,128 B2 | 7/2014 | Hanson et al. |
| 8,835,402 B2 | 9/2014 | Kole et al. |
| 8,865,883 B2 | 10/2014 | Sazani et al. |
| 8,871,918 B2 | 10/2014 | Sazani et al. |
| 8,877,725 B2 | 11/2014 | Iversen et al. |
| 8,969,551 B2 | 3/2015 | Ueda |
| 9,068,185 B2 | 6/2015 | Iversen |
| 9,161,948 B2 | 10/2015 | Hanson |
| 9,249,243 B2 | 2/2016 | Weller et al. |
| 9,278,987 B2 | 3/2016 | Hanson et al. |
| 9,416,361 B2 | 8/2016 | Iversen et al. |
| 9,469,664 B2 | 10/2016 | Hanson et al. |
| 9,499,583 B2 | 11/2016 | Yamada et al. |
| 9,534,220 B2 | 1/2017 | Geller et al. |
| 9,790,499 B2 | 10/2017 | Hanson et al. |
| 9,920,085 B2 | 3/2018 | Hanson |
| 10,017,763 B2 | 7/2018 | Iversen |
| 10,100,305 B2 | 10/2018 | Iversen |
| 2001/0021700 A1 | 9/2001 | Moore et al. |
| 2002/0045736 A1 | 4/2002 | Yu et al. |
| 2002/0127198 A1 | 9/2002 | Rothbard et al. |
| 2003/0022831 A1 | 1/2003 | Rothbard et al. |
| 2003/0031655 A1 | 2/2003 | Woolf |
| 2003/0045488 A1 | 3/2003 | Brown et al. |
| 2003/0087861 A1 | 5/2003 | Iversen |
| 2003/0095953 A1 | 5/2003 | Cabot et al. |
| 2003/0166588 A1 | 9/2003 | Iversen et al. |
| 2003/0171335 A1 | 9/2003 | Stein et al. |
| 2003/0175767 A1 | 9/2003 | Davis et al. |
| 2003/0185788 A1 | 10/2003 | Rothbard et al. |
| 2003/0224353 A1 | 12/2003 | Stein et al. |
| 2003/0228348 A1 | 12/2003 | Hirayama et al. |
| 2004/0072743 A1 | 4/2004 | Christensen et al. |
| 2004/0110296 A1 | 6/2004 | Vargeese et al. |
| 2004/0161844 A1 | 8/2004 | Baker et al. |
| 2004/0170955 A1 | 9/2004 | Arap et al. |
| 2004/0247614 A1 | 12/2004 | Dorr et al. |
| 2004/0259108 A1 | 12/2004 | Linnen et al. |
| 2005/0096291 A1 | 5/2005 | Iversen et al. |
| 2005/0107312 A1 | 5/2005 | Keicher et al. |
| 2005/0171026 A1 | 8/2005 | Hagiwara et al. |
| 2005/0176661 A1 | 8/2005 | Vaillant et al. |
| 2005/0222068 A1* | 10/2005 | Mourich ............ A61K 31/675 514/44 A |
| 2005/0234002 A1 | 10/2005 | Mourich et al. |
| 2006/0014712 A1 | 1/2006 | Neuman |
| 2006/0078542 A1 | 4/2006 | Mah et al. |
| 2006/0104989 A1 | 5/2006 | Edwards et al. |
| 2006/0127981 A1 | 6/2006 | Bergman et al. |
| 2006/0148747 A1 | 7/2006 | Stein et al. |
| 2006/0149046 A1 | 7/2006 | Arar |
| 2006/0269911 A1 | 11/2006 | Iversen et al. |
| 2006/0276425 A1 | 12/2006 | Mourich et al. |
| 2006/0281701 A1 | 12/2006 | Stein et al. |
| 2007/0004661 A1 | 1/2007 | Stein et al. |
| 2007/0021362 A1 | 1/2007 | Geller et al. |
| 2007/0037763 A1 | 2/2007 | Stein et al. |
| 2007/0066556 A1 | 3/2007 | Stein et al. |
| 2007/0082336 A1 | 4/2007 | Johnsson et al. |
| 2007/0129323 A1 | 6/2007 | Stein et al. |
| 2007/0265214 A1 | 11/2007 | Stein et al. |
| 2008/0160225 A1 | 7/2008 | Lowe et al. |
| 2008/0194463 A1 | 8/2008 | Weller et al. |
| 2008/0267978 A1 | 10/2008 | Zutter |

(56) References Cited

U.S. PATENT DOCUMENTS

| | | |
|---|---|---|
| 2009/0075377 A1 | 3/2009 | Lu et al. |
| 2009/0082547 A1 | 3/2009 | Iversen et al. |
| 2009/0099066 A1 | 4/2009 | Moulton et al. |
| 2009/0110689 A1* | 4/2009 | Mourich ............ C12N 15/1138 424/184.1 |
| 2009/0131624 A1 | 5/2009 | Reeves et al. |
| 2009/0131632 A1 | 5/2009 | Fox et al. |
| 2009/0180958 A1 | 7/2009 | Koivistoinen et al. |
| 2009/0318676 A1 | 12/2009 | Manoharan et al. |
| 2010/0016215 A1 | 1/2010 | Moulton et al. |
| 2010/0021456 A1 | 1/2010 | Miossec et al. |
| 2010/0063133 A1 | 3/2010 | Neuman et al. |
| 2010/0105120 A1 | 4/2010 | Zebala |
| 2010/0105865 A1 | 4/2010 | Telford et al. |
| 2010/0130591 A1 | 5/2010 | Sazani et al. |
| 2010/0137408 A1 | 6/2010 | Geller et al. |
| 2010/0184670 A1 | 7/2010 | Mourich et al. |
| 2010/0184833 A1 | 7/2010 | De Kimpe et al. |
| 2010/0190689 A1 | 7/2010 | Thornton et al. |
| 2010/0234280 A1 | 9/2010 | Geller et al. |
| 2010/0234281 A1 | 9/2010 | Weller et al. |
| 2011/0118334 A1 | 5/2011 | Iversen |
| 2011/0224283 A1 | 9/2011 | Iversen |
| 2011/0269665 A1 | 11/2011 | Kole |
| 2011/0289608 A1 | 11/2011 | Schnell et al. |
| 2011/0306550 A1 | 12/2011 | Vitek et al. |
| 2012/0122769 A1 | 5/2012 | Iversen |
| 2012/0141463 A1 | 6/2012 | Wu et al. |
| 2012/0148622 A1 | 6/2012 | tenOever |
| 2012/0289457 A1* | 11/2012 | Hanson ................ A61K 31/713 514/3.1 |
| 2013/0005792 A1 | 1/2013 | Haining et al. |
| 2013/0045202 A1 | 2/2013 | Irving et al. |
| 2013/0089517 A1 | 4/2013 | Brady et al. |
| 2013/0197220 A1 | 8/2013 | Ueda |
| 2013/0289091 A1 | 10/2013 | Geller et al. |
| 2014/0024698 A1 | 1/2014 | Kole et al. |
| 2014/0213737 A1 | 7/2014 | Weller et al. |
| 2014/0296321 A1 | 10/2014 | Iversen |
| 2015/0080311 A1 | 3/2015 | Moulton et al. |
| 2015/0141321 A1 | 5/2015 | Kole et al. |
| 2015/0152415 A1 | 6/2015 | Sazani et al. |

FOREIGN PATENT DOCUMENTS

| | | |
|---|---|---|
| EP | 1 938 802 A1 | 7/2008 |
| JP | H05-504563 A | 7/1993 |
| JP | 2002-167441 A | 4/2002 |
| JP | 2002-511885 A | 4/2002 |
| JP | 2002-540113 A | 11/2002 |
| JP | 2003-521680 A | 7/2003 |
| JP | 2004-537517 A | 12/2004 |
| JP | 2007-536253 A | 12/2007 |
| JP | 2008-509701 A | 4/2008 |
| JP | 2008-513012 A | 5/2008 |
| JP | 2010-505741 A | 2/2010 |
| JP | 2011-505846 A | 3/2011 |
| JP | 2011-217751 A | 11/2011 |
| JP | 2014-515762 A | 7/2014 |
| WO | 91/09033 A1 | 6/1991 |
| WO | 93/01286 A2 | 1/1993 |
| WO | 94/04686 A1 | 3/1994 |
| WO | 97/40854 A2 | 11/1997 |
| WO | 98/03533 A1 | 1/1998 |
| WO | 98/32467 A2 | 7/1998 |
| WO | 00/44897 A1 | 8/2000 |
| WO | 00/56740 A1 | 9/2000 |
| WO | 00/71706 A1 | 11/2000 |
| WO | 01/49775 A2 | 7/2001 |
| WO | 01/62297 A1 | 8/2001 |
| WO | 01/76636 A2 | 10/2001 |
| WO | 02/038764 A2 | 5/2002 |
| WO | 02/079467 A2 | 10/2002 |
| WO | 02/092617 A | 11/2002 |
| WO | 02/094250 A2 | 11/2002 |
| WO | 03/033657 A2 | 4/2003 |
| WO | 03/068942 A2 | 8/2003 |
| WO | 2003/078583 A2 | 9/2003 |
| WO | 2004/097017 A2 | 11/2004 |
| WO | 2005/007805 A2 | 1/2005 |
| WO | 2005/010044 A2 | 2/2005 |
| WO | 2005/030799 A1 | 4/2005 |
| WO | 2005/030800 A2 | 4/2005 |
| WO | 2005/065268 A2 | 7/2005 |
| WO | 2005/072527 A2 | 8/2005 |
| WO | 2005/089247 A2 | 9/2005 |
| WO | 2005/115479 A2 | 12/2005 |
| WO | 2006/000057 A1 | 1/2006 |
| WO | 2006/033933 A2 | 3/2006 |
| WO | 2006/047683 A2 | 5/2006 |
| WO | 2006/050414 A2 | 5/2006 |
| WO | 2006/083183 A1 | 8/2006 |
| WO | 2006/085973 A2 | 8/2006 |
| WO | 2006/086667 A2 | 8/2006 |
| WO | 2006/088833 A2 | 8/2006 |
| WO | 2006/121951 A2 | 11/2006 |
| WO | 2007/002390 A2 | 1/2007 |
| WO | 2007/009094 A2 | 1/2007 |
| WO | 2007/030576 A2 | 3/2007 |
| WO | 2007/030691 A2 | 3/2007 |
| WO | 2007/056466 A2 | 5/2007 |
| WO | 2007/103529 A2 | 9/2007 |
| WO | 2008/005002 A1 | 1/2008 |
| WO | 2008/008113 A1 | 1/2008 |
| WO | 2008/018795 A1 | 2/2008 |
| WO | 2008/025025 A2 | 2/2008 |
| WO | 2008/036127 A2 | 3/2008 |
| WO | 2008/036406 A3 | 3/2008 |
| WO | 2009/005793 A2 | 1/2009 |
| WO | 2009/026412 A1 | 2/2009 |
| WO | 2009/064471 A1 | 5/2009 |
| WO | 2009/086469 A2 | 7/2009 |
| WO | 2009/144481 A2 | 12/2009 |
| WO | 2010/019847 A2 | 2/2010 |
| WO | 2010/048586 A1 | 4/2010 |
| WO | 2010/054267 A1 | 5/2010 |
| WO | 2010/080554 A1 | 7/2010 |
| WO | 2010/120820 A1 | 10/2010 |
| WO | 2010/148249 A1 | 12/2010 |
| WO | 2011/060320 A1 | 5/2011 |
| WO | 2011/143608 A1 | 11/2011 |
| WO | 2011/150408 A2 | 12/2011 |
| WO | 2012/150960 A1 | 11/2012 |
| WO | 2013/142087 A1 | 9/2013 |

OTHER PUBLICATIONS

Tripp et al., TH 1- and TH2-type cytokine expression by activated T lymphocytes from the lung and spleen during the inflammatory response to respiratory syncytial virus, Cytokine, vol. 12, pp. 801-807. (Year: 2000).*

Hanley et al., Preferential killing of cancer cells and activated human T cells using ZnO nanoparticles, Nanotechnology, vol. 9, pp. 1-10. (Year: 2008).*

Abes et al., "Delivery of steric block morpholino oligomers by (R-X-R)$_4$ peptides: structure-activity studies," *Nucleic Acids Research* 36(20):6343-6354, 2008.

Abes et al., "Arginine-rich cell penetrating peptides: Design, structure-activity, and applications to alter pre-mRNA splicing by steric-block oligonucleotides," *Journal of Peptide Science* 14:455-460, 2008.

Abes et al., "Vectorization of morpholino oligomers by the (R-Ahx-R)$_4$ peptide allows efficient splicing correction in the absence of endosomolytic agents," *Journal of Controlled Release* 116:304-313, 2006.

Agrawal et al., "Oligodeoxynucleoside phosphoramidates and phosphorothioates as inhibitors of human immunodeficiency virus," *Proc. Natl. Acad. Sci. USA* 85:7079-7083, 1988.

Agrawal et al., "Site-specific excision from RNA by RNase H and mixed-phosphate-backbone oligodeoxynucleotides," *Proc. Natl. Acad. Sci. USA* 87:1401-1405, 1990.

(56) References Cited

OTHER PUBLICATIONS

Agrawal et al., "Antisense therapeutics: is it as simple as complementary base recognition?" Molecular Med. Today 6:72-81, 2000.
Agrawal, "Antisense oligonucleotides: towards clinical trials," Tibtech 14(10):376-387, 1996.
Akhtar et al., "Interactions of antisense DNA oligonucleotide analogs with phospholipid membranes (liposomes)," Nucleic Acids Res. 19(20)5551-5559, 1991.
Alter et al., "Systemic delivery of morpholino oligonucleotide restores dystrophin expression bodywide and improves dystrophic pathology," Nature Medicine 12(2):175-177, 2006.
Anderson et al., "Inhibition of Human Cytomegalovirus Immediate-Early Gene Expression by an Antisense Oligonucleotide Complementary to Immediate-Early RNA," Antimicrobial Agents and Chemotherapy 40(9):2004-2011, 1996.
Anderson et al., "Distribution of Equilibrative, Nitrobenzylthioinosine-Sensitive Nucleoside Transporters (ENT1) in Brain," Journal of Neurochemistry 73(2):867-873, 1999.
Andreasen et al., "Expression and Functional Importance of Collagen-Binding Integrins α1β1 and α2β1, on Virus-Activated T Cells," The Journal of Immunology 171:2804-2811, 2003.
Arora et al., "Bioavailability and Efficacy of Antisense Morpholino Oligomers Targeted to c-myc and Cytochrome P-450 3A2 Following Oral Administration in Rats," Journal of Pharmaceutical Sciences 91(4):1009-1018, 2002.
Arya et al., "Triple-helix formation of DNA oligomers with methylthiourea-linked nucleosides (DNmt): A kinetic and thermodynamic analysis," Proc. Natl. Acad. Sci. USA 96:4384-4389, 1999.
Astriab-Fisher et al., "Antisense Inhibition of P-glycoprotein Expression Using Peptide-Oligonucleotide Conjugates," Biochemical Pharmacology 60:83-90, 2000.
Astriab-Fisher et al., "Conjugates of Antisense Oligonucleotides with the Tat and Antennapedia Cell-Penetrating Peptides: Effects on Cellular Uptake, Binding to Target Sequences, and Biologic Actions," Pharmaceutical Research 19(6):744-754, 2002.
Bailey et al., "Cationic oligonucleotides can mediate specific inhibition of gene expression in Xenopus oocytes," Nucleic Acids Research 26(21):4860-4867, 1998.
Banerjee et al., "Interaction of picornavirus 2C polypeptide with the viral negative-strand RNA," Journal of General Virology 82:2621-2627, 2001.
Banerjee et al., "Interaction of Poliovirus-Encoded 2C/2BC Polypeptides with the 3' Terminus Negative-Strand Cloverleaf Requires an Intact Stem-Loop b," Virology 280:41-51, 2001.
Banerjee et al., "Poliovirus-Encoded 2C Polypeptide Specifically Binds to the 3'-Terminal Sequences of Viral Negative-Strand RNA," Journal of Virology 71(12):9570-9578, 1997.
Banerjee et al., "Specific Interaction of Hepatitis C Virus Protease/Helicase NS3 with the 3'Terminal Sequences of Viral Positive- and Negative-Strand RNA," Journal of Virology 75(4):1708-1721, 2001.
Barawkar et al., "Synthesis, biophysical properties, and nuclease resistance properties of mixed backbone oligodeoxynucleotides containing cationic internucleoside guanidinium linkages: Deoxynucleic guanidine/DNA chimeras," Proc. Natl. Acad. Sci. USA 95:11047-11052, 1998.
Basler et al., "The Ebola virus VP35 protein functions as a type I IFN antagonist," PNAS 97(22):12289-12294, 2000.
Berthet F-X et al. "Characterization of the Mycobacterium tuberculosis erp gene encoding a potential cell surface protein with repetitive structures," Microbiology 141:2123-2130, 1995.
Blattman et al., "Therapeutic use of IL-2 to enhance antiviral T-cell responses in vivo," Nature Medicine 9(5):540-547, 2003.
Blommers et al., "An approach to the structure determination of nucleic acid analogues hybridized to RNA. NMR studies of a duplex between 2'-Ome RNA and oligonucleotide containing a single amide backbone modification," Nucleic Acids Research 22(20): 4187-4194, 1994.
Bonham et al., "An assessment of the antisense properties of RNase H-competent and steric-blocking oligomers," Nucleic Acids Research 23(7):1197-1203, 1995.

Borio et al., "Hemorrhagic Fever Viruses as Biological Weapons: Medical and Public Health Management," JAMA 287(18):2391-2405, 2002.
Borriello et al., "Differential Expression of Alternate mB7-2 Transcripts," The Journal of Immunology 155(12):5490-5497, 1995.
Boudvillain et al., "Transplatin-Modified Oligo(2'-O-methyl ribonucleotide)s: A New Tool for Selective Modulation of Gene Expression," Biochemistry 36(10):2925-2931, 1997.
Bramhill, "Bacterial Cell Division," Annu. Rev. Cell Dev. Biol. 13:395-424, 1997.
Branch, "A good antisense molecule is hard to find," Trends in Biochem. Sci. 23:45-50, 1998.
Brasey et al., "The Leader of Human Immunodeficiency Virus Type 1 Genomic RNA Harbors an Internal Ribosome Entry Segment That Is Active During the $G_2$/M Phase of the Cell Cycle," Journal of Virology 77(7):3939-3949, 2003.
Bray et al., "A Mouse Model for Evaluation of Prophylaxis and Therapy of Ebola hemorrhagic Fever," The Journal of Infectious Diseases 178:651-661, 1998.
Burnett et al., "The Evolving Field of Biodefence: Therapeutic Developments and Diagnostics," Natural Reviews | Drug Discovery 4:281-297, 2005.
Burrer et al., "Antiviral Effects of Antisense Morpholino Oligomers in Murine Coronavirus Infection Models," Journal of Virology 81(11):5637-5648, 2007.
Carlson et al., "In vitro-differentiated TH17 cells mediate lethal acute graft-versus-host disease with severe cutaneous and pulmonary pathologic manifestations," Blood 113(6): 1365-1374, 2009.
Chambers et al., "CTLA-4-Mediated Inhibition in Regulation of T Cell Responses: Mechanisms and Manipulation in Tumor Immunotherapy," Annu. Rev. Immunol. 19:565-594, 2001.
Chen et al., "A Concise Method for the Preparation of Peptide and Arginine-Rich Peptide-Conjugated Antisense Oligonucleotide," Bioconjugate Chem. 14:532-538, 2003.
Chirila et al., "The use of synthetic polymers for delivery of therapeutic antisense oligodeoxynucleotides," Biomaterials 23:321-342, 2002.
Clarke et al., "Organization and Expression of Calicivirus Genes," Journal of Infectious Diseases 181(Suppl. 2):S309-S316, 2000.
Connolly et al., "Pathogenesis of Experimental Ebola Virus Infection in Guinea Pigs," The Journal of Infectious Diseases 179(Suppl. 1):S203-S217, 1999.
Corey et al., "Morpholino antisense oligonucleotides: tools for investigating vertebrate development," Genome Biology 2(5):reviews 1015.1-1015.3, 2001.
Crooke, Antisense Research And Application, ed. Springer, 1998, Chapter 1, "Basic Principles of Antisense Therapeutics," pp. 1-50. (52 pages).
Crooke, Stanley (ed.), Antisense Drug Technology: Principles, Strategies, and Applications, CRC Press, New York, 2001, Chap. 5, "Methods of Selecting Sites in RNA for Antisense Targeting," pp. 107-118. (14 pages).
Cross et al., "Solution structure of an RNA x DNA hybrid duplex containing a 3'-Thioformacetal Linker and an RNA A-tract," Biochemistry 36:4096-4107, 1997.
Dagle et al., "Targeted elimination of zygotic messages in Xenopus laevis embryos by modified oligonucleotides possessing terminal cationic linkages," Nucleic Acids Research 28(10):2153-2157, 2000.
Dapić et al., "Biophysical and biological properties of quadruplex oligodeoxyribonucleotides," Nucleic Acids Research 31(8):2097-2107, 2003.
De Mendonca-Lima L et al., "The allele encoding the mycobacterial Erp protein affects lung disease in mice," Cellular Microbiology, Jan. 22, 2003, p. 65-73.
Deas et al., "Inhibition of Flavivirus Infections by Antisense Oligomers Specifically Suppressing Viral Translation and RNA Replication," Journal of Virology 79(8):4599-4609, 2005.
Deere et al., "Antisense Phosphorodiamidate Morpholino Oligomer Length and Target Position Effects on Gene-Specific Inhibition in Escherichia coli," Antimicrobial Agents and Chemotherapy 49(1): 249-255, Jan. 2005.

(56) References Cited

OTHER PUBLICATIONS

Dempcy et al., "Design and synthesis of deoxynucleic guanidine: A polycation analogue of DNA," *Proc. Natl. Acad. Sci. USA 91*:7864-7868, 1994.
Dempcy et al., "Design and synthesis of ribonucleic guanidine: A polycationic analog of RNA," *Proc. Natl. Acad. Sci. USA 93*:4326-4330, 1996.
Derossi et al., "Trojan peptides: the penetratin system for intracellular delivery," *Trends in Cell Biology 8*(2):84-87, 1998.
Devi et al., "In vivo bioavailability and pharmacokinetics of a c-MYC antisense phosphorodiamidate morpholino oligomer, AVI-4126, in solid tumors," *Clin. Cancer Res. 11*(10):3930-3938, 2005. (10 pages).
Devi et al., "Inhibition of Human Chorionic Gonadotropin β-Subunit Modulates the Mitogenic Effect of c-myc in Human Prostate Cancer Cells," *The Prostate 53*:200-210, 2002.
Devi, "Prostate cancer: Status of current treatments and emerging antisense-based therapies," *Current Opinion in Molecular Therapeutics 4*(2):138-148, 2002.
Ding et al., "An oligodeoxyribonucleotide N3'→P5' phosphoramidate duplex forms an A-type helix in solution," Nucleic Acids Research 24(2):354-360, 1996.
Donachie, "The Cell Cycle of *Escherichia coli*," *Annu. Rev. Microbiol. 47*: 199-230, 1993. (34 pages).
Dryselius et al., "The Translation Start Codon Region Is Sensitive to Antisense PNA Inhibition in *Escherichia coli*," *Oligonucleotides 13*: 427-433, 2003.
Egholm et al., "PNA hybridizes to complementary oligonucleotides obeying the Watson-Crick hydrogen-bonding rules," *Nature 365*(6446):566-568, 1993.
Egli et al., "Probing the Influence of Stereoelectronic Effects on the Biophysical Properties of Oligonucleotides: Comprehensive Analysis of the RNA Affinity, Nuclease Resistance, and Crystal Structure Ten 2'-O-Ribonucleic Acid Modifications," *Biochemistry 44*:9045-9057, 2005.
EMBL/GenBank/DDBJ database (DESHAZER), Sequence CH899747. 1, retrieved from the Internet, URL=http://www.ebi.ac.uk/sgibin/emblfetch?style+html&id+CH899747, download date May 26, 2007, 196 pages.
Eriksson et al., "Cell Permeabilization and Uptake of Antisense Peptide-Peptide Nucleic Acid (PNA) into *Escherichia coli*," *Journal of Biological Chemistry 277*(9):7144-7147, Mar. 1, 2002.
Ex Parte Thumm, 132 USPQ 66 (1961), 3 pages.
Feldmann et al., "Classification, Structure, and Replication of Filoviruses," *Curr. Top. Microbiol. Immunol. 235*:1-21, 1999.
Feldmann et al., "EBOLA virus: from discovery to vaccine," *Nature Reviews 3*(8):677-685, 2003.
Feldmann et al., "Molecular biology and evolution of filoviruses," *Arch. Virol. 7*(Suppl.):81-100, 1993.
Felgner et al., "Lipofection: A highly efficient, lipid-mediated DNA-transfection procedure," *Proc. Natl. Acad. Sci. USA 84*(21):7413-7417, 1987.
Gait et al., "Synthetic Analogues of Polynucleotides. Part XII. Synthesis of Thymidine Derivatives containing an Oxyacetamido- or an Oxyformamido-linkage instead of a Phosphodiester Group," *J. Chem. Soc.* [Perkin 1] 0(14): 1684-1686, 1974.
Galloway et al., "A Mutant of *Escherichia coli* Defective in the First Step of Endotoxin Biosynthesis," *J. Biol. Chem. 265*(11):6394-6402, 1990.
Ge et al., "Inhibition of Multiple Subtypes of Influenza A Virus in Cell Cultures with Morpholino Oligomers," *Antimicrobial Agents and Chemotherapy 50*(11):3724-3733, 2006.
Gebski et al., "Morpholino antisense oligonucleotide induced dystrophin exon 23 skipping in mdx mouse muscle," *Human Molecular Genetics 12*(15):1801-1811, 2003.
Gee et al., "Assessment of High-Affinity Hybridization, RNase H Cleavage, and Covalent Linkage in Translation Arrest by Antisense Oligonucleotides," *Antisense & Nucleic Acid Drug Development 8*:103-111, 1998.

Geisbert et al., "Ebola virus: new insights into disease aetiopathology and possible therapeutic interventions," *Expert Reviews in Molecular Medicine 6*(20):1-24, 2004.
Geisbert et al., "Treatment of Ebola virus infection with a recombinant inhibitor of factor VIIa/tissue factor: a study in rhesus monkeys," *The Lancet 362*(9400):1953-1958, 2003.
Geller et al., "Antisense Antibacterial Method and Compound," Office Action dated Sep. 29, 2010, U.S. Appl. No. 11/173,847, 25 pages.
Geller et al., "Antisense phosphorodiamidate morpholino oligomer inhibits viability of *Escherichia coli* in pure culture and in mouse peritonitis," *Journal of Antimicrobial Chemotherapy 55*:938-988, 2005.
Geller et al., "Inhibition of Gene Expression in *Escherichia coli* by Antisense Phosphorodiamidate Morpholino Oligomers," *Antimicrobial Agents and Chemotherapy 47*(10):3233-3239, 2003.
Geller et al., "Translocation of Pro-OmpA across Inner Membrane Vesicles of *Escherichia coli* Occurs in Two Consecutive Energetically Distinct Steps," *The Journal of Biological Chemistry 264*(28):16465-16469, 1989.
GenBank Accession No. AB011549, retrieved Jul. 15, 2010, from http://www.ncbi.nlm.nih.gov/nuccore/4589740. 35 pages.
GenBank Accession No. AF074613, retrieved Jul. 15, 2010, from http//www.ncbi.nlm.nih.gov/nuccore/3822114. 45 pages.
GenBank Accession No. AJ007716, retrieved Jul. 15, 2010, from http://www.ncbi.nlm.nih.gov/nuccore/4775309. 4 pages.
GenBank Accession No. X97542, retrieved Jul. 15, 2010, from http://www.ncbi.nlm.nih.gov/nuccore/2244635. 4 pages.
GenBank Accession No. Y11275, retrieved Jul. 15, 2010, from http://www.ncbi.nlm.nih.gov/nuccore/4127812. 4 pages.
Gerdes et al., "Experimental Determination and System Level Analysis of Essential Genes in *Escherichia coli* MG1655," *Journal of Bacteriology 185*(19):5673-5684, 2003.
Ghosh et al., "Intracellular Delivery Strategies for Antisense Phosphorodiamidate Morpholino Oligomers," *Antisense & Nucleic Acid Drug Development 10*:263-274, 2000.
Gilbert et al., "Sieve analysis: methods for assessing from vaccine trial data how vaccine efficacy varies with genotypic and phenotypic pathogen variation," *J Clinical Epidemiology 54*:68-85, 2001.
Gong et al., "Molecular Mechanisms in Morpholino—DNA Surface Hybridization," *J. Am. Chem. Soc. 132*:9663-9671, 2010.
Good et al., "Antisense inhibition of gene expression in bacteria by PNA targeted to mRNA," Nature Biotech 16: 355-358, Apr. 1998.
Good et al., "Antisense PNA effects in *Escherichia coli* are limited by the outer-membrane LPS layer," *Microbiology 149*:2665-2670, 2000.
Good et al., "Bactericidal antisense effects of peptide-PNA conjugates," *Nature Biotechnology 19*(4):360-364, 2001.
Good et al., "Inhibition of translation and bacterial growth by peptide nucleic acid targeted to ribosomal RNA," *Proc. Natl. Acad. Sci. USA 95*(5):2073-2076, 1998.
Green et al., "Antisense Oligonucleotides: An Evolving Technology for the Modulation of Gene Expression in Human Disease," *J. Am. Coll. Surg. 191*:93-105, 2000.
Greenberg et al., "Antisense Phosphorodiamidate Morpholino Oligmers Targeted to an Essential Gene Inhibit *Burkholderia cepacia* Complex," *The Journal of Infectious Diseases 201*(12): 000-000, 2010 (9 pages).
Gupta, "Molecular signaling in death receptor and mitochondrial pathways of apoptosis (Review)," *International Journal Of Oncology 22*(1):15-20, 2003.
Hale et al., "Recruitment of ZipA to the Septal Ring of *Escherichia coli* is Dependent on FtsZ and Independent of FtsA," *Journal of Bacteriology 181*(1): 167-176, 1999.
Hames et al. (eds.), *Nucleic acid hybridization: a practical approach*, IRL Press, Oxford, England, pp. 107-108, 1985, 12 pages.
Hanecak et al., "Antisense Oligonucleotide Inhibition of Hepatitis C Virus Gene Expression in Transformed Hepatocytes," *Journal of Virology 70*(8):5203-5212, 1996.
He et al., "A Comparison of in Vitro and in Vivo Stability in Mice of Two Morpholino Duplexes Differing in Chain Length," *Bioconjugte Chem. 14*:1018-1023, 2003.

(56) References Cited

OTHER PUBLICATIONS

Heineke et al., "Genetic Deletion of Myostatin From the Heart Prevents Skeletal Muscle Atrophy in Heart Failure," *Circulation* 121:419-425, 2010.
Holland, Morse (ed.), *Emerging Viruses*, Oxford University Press US, New York, 1993, Chap. 19, "Replication Error, Quasispecies Populations, and Extreme Evolution Rates of RNA Viruses," pp. 203-218. (18 pages).
Hudziak et al., "Antiproliferative Effects of Steric Blocking Phosphorodiamidate Morpholino Antisense Agents Directed Against C-MYC," Antisense & Nucleic Acid Drug Development 10 (3): 163-176, Jun. 2000.
Hudziak et al., "Resistance of Morpholino Phosphorodiamidate Oligomers to Enzymatic Degradation," *Antisense & Nucleic Acid Drug Development* 6:267-272, 1996.
Hunt et al., "Identification of *Burkholderia cenocepacia* Genes Required for Bacterial Survival In Vivo," *Infection and Immunity* 72(7):4010-4022, 2004.
International Preliminary Examination Report for PCT/US2004/013660, dated Nov. 4, 2005, 8 pgs.
International Preliminary Report on Patentability for corresponding International Application No. PCT/US2008/008168, dated Oct. 12, 2009, 10 pgs.
International Preliminary Report on Patentability for International Application No. PCT/US2005/018213, dated Oct. 23, 2007, 7 pages.
International Search Report (U.S.), dated Aug. 11, 2006, for PCT/US05/023553, 5 pages.
International Search Report (U.S.), dated Oct. 12, 2001, for PCT/US01/00222, 9 pages.
International Search Report and Written Opinion for International Application No. PCT/US2005/018213, dated Sep. 26, 2007, 7 pgs.
International Search report and Written Opinion, dated Mar. 19, 2009, for PCT/US08/08168, 11 pages.
International Search Report, dated Feb. 21, 2005, for PCT/US2004/013660, 6 pages.
Iversen et al., "Splice-Region Antisense Composition and Method," Office Action mailed on Apr. 23, 2010, U.S. Appl. No. 11/433,214, 17 pages.
Iversen et al., "Antisense Antiviral Compound and Method for Treating ssRNA Viral Infection," Office Action mailed Oct. 19, 2010, U.S. Appl. No. 11/432,031, 25 pages.
Iversen, "Phosphorodiamidate Morpholino Oligomers," in Crooke (ed.), *Antisense Drug Technology*, Marcel Dekker, Inc., New York, 2001, pp. 375-389, 17 pages.
Iversen, "Phosphorodiamidate morpholino oligomers: Favorable properties for sequence-specific gene inactivation," *Current Opinion in Molecular Therapeutics* 3(3):235-238, 2001.
Jackowski et al., "Ratio of Active to Inactive Forms of Acyl Carrier Protein in *Escherichia coli*," *J. Biol. Chem.* 258(24):15186-15191, 1983.
Jackson et al., "*Escherichia coli* O157:H7 diarrhoea associated with well water and infected cattle on an Ontario farm," *Epidemiol Infect* 120(1): 17-20, 1998.
Jaeger et al., "Improved predictions of secondary structures for RNA," *Proc. Natl. Sci. USA* 86:7706-7710, 1989.
Jahrling et al., "Evaluation of Immune Globulin and Recombinant Interferon-α2b for Treatment of Experimental Ebola Virus Infections," *The Journal of Infectious Diseases* 179(Suppl 1):S224-S234, 1999.
Jayaraman et al., "Selective inhibition of *Escherichia coli* protein synthesis and growth by nonionic oligonucleotides complementary to the 3' end of 16S rRNA," *Proc Natl Acad Sci USA* 78(3): 1537-1541, 1981.
Jearawiriyapaisarn et al., "Sustained Dystrophin Expression Induced by Peptide-conjugated Morpholino Oligomers in the Muscles of mdx Mice," *Mol. Ther.* 16(9):1624-1629, 2008.
Jen et al., "Suppression of Gene Expression by Targeted Disruption of Messenger RNA: Available Options and Current Strategies," *Stem Cells* 18:307-319, 2000.

Johannes et al., "Identification of eukaryotic mRNAs that are translated at reduced cap binding complex eIF4F concentrations using a cDNA microarray." *PNAS* 96(23):13118-13123, 1999.
Joseleau-Petit et al., "Metabolic Alarms and Cell Division in *Escherichia coli*," *J Bacteriology* 181(1): 9-14, 1999.
Jubin et al., "Hepatitis C Virus Internal Ribosome Entry Site (IRES) Stem Loop IIId Contains a Phylogenetically Conserved GGG Triplet Essential for Translation and IRES Folding," *Journal of Virology* 74(22):10430-10437, 2000.
Kang et al., "Stacking Interactions of ApA Analogues with Modified Backbones," *Biopolymers* 32:1351-1363, 1992.
Kang et al., "Up-Regulation of Luciferase Gene Expression with Antisense Oligonucleotides: Implications and Applications in Functional Assay Development," *Biochemistry* 37:6235-6239, 1998.
Knapp et al., "Resistance to chemotherapeutic drugs overcome by c-Myc inhibition in a Lewis lung carcinoma murine model," *Anti-Cancer Drugs* 14:39-47, 2003.
Knudsen et al., "Antisense properties of duplex- and triplex-forming PNAs," *Nucleic Acids Res* 24(3):494-500, 1996.
Kolonin et al., "Synchronous selection of homing peptides for multiple tissues by in vivo phage display," *The FASEB Journal* 20(7):979-981, 2006.
Kumar et al., "Antisense RNA: Function and Fate of Duplex RNA in Cells of Higher Eukaryotes," *Microbiology and Molecular Biology Reviews* 62(4):1415-1434, 1998.
Lappalainen et al., "Cationic liposomes mediated delivery of antisense oligonucleotides targeted to HPV 16 E7 mRNA in CaSki cells," *Antiviral Research* 23:119-130, 1994.
Lebleu et al., "Cell penetrating peptide conjugates of steric block oligonucleotides," *Advanced Drug Delivery Reviews* 60:517-529, 2008.
Lesnikowski et al., "Octa(thymidine methanephosphonates) of partially defined stereochemistry: Synthesis and effect of chirality at phosphorus on binding to pentadecadeoxyriboadenylic acid," *Nucleic Acids Research* 18(8): 2109-2115, 1990.
Lesnikowski et al., "Octa(thymidine methanephosphonats) of partially defined stereochemistry: synthesis and effect of chirality at phosphorous on binding to pentadecadeoxyriboadenylic acid," *Nucleic Acids Res.* 18(8):2109-2115, 1990.
Li et al., "Folate-Mediated Targeting of Antisense Oligodeoxynucleotides to Ovarian Cancer Cells," *Pharmaceutical Research* 15(10):1540-1545, 1998.
Linkletter et al., "Solid-phase synthesis of oligopurine deoxynucleic guanidine (DNG) and analysis of binding with DNA oligomers," *Nucleic Acids Research* 29(11):2370-2376, 2001.
Linkletter et al., "Solid-phase Synthesis of Positively Charged Deoxynucleic Guanidine (DNG) Modified Oligonucleotides Containing Neutral Urea Linkages: Effect of Charge Deletions on Binding and Fidelity," *Bioorganic & Medicinal Chemistry* 8:1893-1901, 2000.
Loke et al., "Characterization of oligonucleotide transport into living cells," *Proc. Natl. Acad. Sci USA* 86(10):3474-3478, 1989.
Lopez De Quinto et al., "Involvement of the Aphthovirus RNA Region Located between the Two Functional AUGs in Start Codon Selection," *Virology* 255(2):324-336, 1999.
Lu et al., "Therapeutic dendritic-cell vaccine for chronic HIV-1 infection," *Nat. Med.* 10(12):1359-1365, 2004.
Lutkenhaus et al., "Bacterial Cell Division and the Z Ring," *Annu. Rev. Biochem.* 66:93-116, 1997. (26 pages).
Manoharan, "Oligonucleotide Conjugates as Potential Antisense Drugs with Improved Uptake, Biodistribution, Targeted Dlivery, and Mechanism of Action," *Antisense & Nucleic Acid Drug Development* 12:103-128, 2002.
Markoff, "5'- and 3'-noncoding regions in flavivirus RNA," *Adv. Virus Res.* 59:177-228, 2003.
Marshall et al., "Arginine-rich cell-penetrating peptides facilitate delivery of antisense oligomers into murine leukocytes and alter pre-mRNA splicing," *Journal of Immunological Methods* 325:114-126, 2007.
Matsui et al., "Protein Therapy: In Vivo Protein Transduction by Polyarginine (11R) PTD and Subcellular Targeting Delivery," *Current Protein and Peptide Science* 4:151-157, 2003.

(56) References Cited

OTHER PUBLICATIONS

Meade et al., "Exogenous siRNA delivery using peptide transduction domains/cell penetrating peptides," *Advanced Drug Delivery Reviews* 59:134-140, 2007.
Mellbye et al., "Variations in Amino Acid Composition of Antisense Peptide-Phosphorodiamidate Morpholino Oligomer Affect Potency against *Escherichia coli* In Vitro and In Vivo," *Antimicrobial Agents and Chemotherapy* 53(2):525-530, 2009.
Mertes et al., "Synthesis of Carbonate Analogs of Dinucleosides. 3'-Thymidinyl 5'-thymidinyl Carbonate, 3'-Thymidinyl 5'-(5-Fluoro-2'-deoxyuridinyl) Carbonate, and 3'-(5-Fluoro-2'-deoxyuridinyl) 5'-Thymidinyl Carbonate," *J. Med. Chem.* 12(1):154-157, 1969.
Meyer et al., "Arenaviruses: Geonomic RNAs, Transcription, and Replication," *Curr. Top. Microbiol. Immunol.* 262:139-157, 2002.
Micklefield, "Backbone Modification of Nucleic Acids: Synthesis, Structure and Therapeutic Applications," *Current Medicinal Chemistry* 8:1157-1179, 2001.
Mitev et al., "Inhibition of Intracellular Growth of *Salmonella enteric* Serovar Typhimurium in Tissue Culture by Antisense Peptide-Phosphorodiamidate Morpholino Oligomer," *Antimicrobial Agents and Chemotherapy* 53(9): 3700-3704, 2009.
Miyada et al., "[6] Oligonucleotide Hybridization Techniques," *Methods in Enzymology* 154:94-107, 1987.
Mizutani et al "Enhancement of Sensitivity of Urinary Bladder Tumor Cells to Cisplatin by c-myc Antisense Oligonucleotide," *Cancer* 74:2546-2554, 1994.
Mohamadzadeh et al., "Dentritic cells: In the forefront of immunopathogenesis and vaccine development—A review," *Journal of Immune Based Therapies and Vaccines* 2(1):1-11, 2004.
Morcos, "Achieving Efficient Delivery of Morpholino Oligos in Cultured Cells," *Genesis* 30:94-102, 2001.
Moskophidis et al., "Resistance of Lymphocytic Choriomeningitis Virus to Alpha/Beta Interferon and to Gamma Interferon," *Journal of Virology* 68(3):1951-1955, Mar. 1994.
Moskophidis et al., "Role of virus and host variables in virus persistence or immunopathological disease caused by a noncytolytic virus," *Journal of General Virology* 76:381-391, 1995.
Moulton et al., "Delivery of Antisense Phosphorodiamidate Morpholino Oligomers by Arginine-Rich Peptides," in Proceedings of the 226th ACS National Meeting, Abstract No. 75, American Chemical Society, New York, NY, Sep. 7-11, 2003, 2 pages.
Moulton et al., "Abstracts of Papers: Part 1, Delivery of Antisense Phosphorodiamidate Morpholino Oligomers by Arginine-Rich Peptides", in *Proceedings of the 226th ACS National Meeting*, Biol., American Chemical Society, New York, NY, Sep. 7-11, 2003.
Moulton et al., "Cellular Uptake of Antisense Morpholino Oligomers Conjugated to Arginine-Rich Peptides," *Bioconjugate Chem.* 15:290-299, 2004.
Moulton et al., "Morpholinos and their peptide conjugates: Therapeutic promise and challenge for Duchenne muscular dystrophy," *Biochimica et Biophysica Acta* 1798:2296-2303, 2010.
Moulton et al., "HIV Tat Peptide Enhances Cellular Delivery of Antisense Morpholino Oligomers," *Antisense Nucleic Acid Drug Dev.* 13:31-43, 2003.
Moulton et al., "Peptide-assisted delivery of steric-blocking antisense oligomers," *Curr. Opin. Mol. Ther.* 5(2): 123-132, 2003.
Mourich et al., "Antisense compound and method for selectively killing activated T cells," U.S. Appl. No. 60/505,418, filed Sep. 23, 2003, 60 pgs.
Nasevicius et al., "Effective targeted gene 'knockdown' in zebrafish," *Nature Genetics* 26:216-220, Oct. 2000.
Nekhotiaeva et al., "Inhibition of *Staphylococcus aureus* Gene Expression and Growth Using Antisense Peptide Nucleic Acids," *Molecular Therapy* 10(4):652-659, 2004.
Nelson et al., "Arginine-Rich Peptide Conjugation to Morpholino Oligomers: Effects on Antisense Activity and Specificity," *Bioconjugate Chem.* 16:959-966, 2005.
Neuman et al., "Antisense Morpholino-Oligomers Directed against the 5' end of the Genome Inhibit Coronavirus Proliferation and Growth," *Journal of Virology* 78(11):5891-5899, 2004.
Nielsen, "Peptide nucleic acids as antibacterial agents via the antisense principle," *Exp. Opin. Invest. Drugs* 10(2):331-341, 2001.
Nielsen, "Peptide Nucleic Acids: on the Road to New Gene Therapeutic Drugs," *Pharmacol. Toxicol.* 86(1): 3-7, 2000.
Nielsen et al., "Sequence-Selective Recognition of DNA by Strand Displacement with a Thymine-Substituted Polyamide," *Science* 254(5037): 1497-1500, 1991.
Nikaido, "Transport across the Bacterial Outer Membrane," *J Bioenerg Biomembr* 25(6):581-589, 1993.
O'Ryan et al., Specter et al. (eds.), *Clinical Virology Manual*, Elsevier, New York, 1992, Chapter 22, "Rotavirus, Enteric, Adenoviruses, Norwalk Virus, and Other Gastroenteritis Tract Viruses," pp. 361-396.
Orabona et al., "CD28 induces immunostimulatory signals in dendritic cells via CD80 and CD86," *Nature Immunology* 5(11):1134-1142, 2004.
Orr et al., "Patent review: Therapeutic applications for antisense oligonucleotides 1999-2000" *Current Opinion in Molecular Therapeutics* 2(3):325-331, 2000.
Palù et al. "In pursuit of new developments for gene therapy of human diseases," *Journal of Biotechnology* 68:1-13, 1999.
Pardigon et al., "Cellular Proteins Bind to the 3' end of Sindbis Virus Minus-Strand RNA," *Journal of Virology* 66(2):1007-1015, 1992.
Pardigon et al., "Multiple Binding Sites For Cellular Proteins in the 3' end of Sindbis Alphavirus Minus-Sense RNA," *Journal of Virology* 67(8):5003-5011, 1993.
Pari et al., "Potent Antiviral Activity of an Antisense Oligonucleotide Complementary to the Intron-Exon Boundary of Human Cytomegalovirus Genes UL36 and UL37," *Antimicrobial Agents and Chemotherapy* 39(5):1157-1161, 1995.
Park et al., "Peroxisome Proliferator-Activated Receptor γ Agonist Down-Regulates IL-17 Expression in a Murine Model of Allergic Airway Inflammation," *The Journal of Immunology* 183:3259-3267, 2009.
Partridge et al., "A Simple Method for Delivering Morpholino Antisense Oligos into the Cytoplasm of Cells," *Antisense & Nucleic Acid Drug Dev.* 6:169-175, 1996.
Paul, Semler et al. (eds.), *Molecular Biology of Picornaviruses*, ASM Press, Wastington, DC, 2002, Chap. 19, "Possible Unifying Mechanism of Picornavirus Genome Replication," pp. 227-246.
Peters et al., "An Introduction to Ebola: The Virus and the Disease," *J. Infect. Dis.* 179(Suppl 1)ix-xvi, 1999.
Petersen et al., "Synthesis of Thymidine Dimers Containing Piperazine in the Internucleoside Linkage and their Incorporation into Oligodeoxynucleotides," *Tetrahedron* 51(7):2145-2154, 1995.
Pihl-Carey, "Disease Drug Fails in Phase III," BioWorld Today 10: 1-2, Dec. 1999.
Polacco et al., "A Mutant of *Escherichia coli* Conditionally Defective in the Synthesis of Holo-[Acyl Carrier Protein]," *J. Biol. Chem.* 256(11):5750-5754, 1981.
Polyak et al., "5' Termini of Pichinde Arenavirus S RNAs and mRNAs Contain Nontemplated Nucleotides," *Journal of Virology* 69(5):3211-3215, 1995.
PubChem (online), 6-Aminocaproic Acid—Compound Summary (CID 5460263), retrieved from URL=http://pubchem.ncbi.nlm.nih.gov/summary/summary.cgi?cid=5460263&loc=ec_rcs, download date Jun. 3, 2010, 3 pages.
Qin et al., "In Vivo Evaluation of a Morpholino Antisense Oligomer Directed Against Tumor Necrosis Factor-α," *Antisense & Nucleic Acid Drug Development* 10:11-16, 2000.
Rahman et al., "Antibacterial Activity and Inhibition of Protein Synthesis in *Escherichia coli* by Antisense DNA Analogs," *Antisense Research and Development* 1(4): 319-327, 1991.
Rangachari et al., "T-bet negatively regulates autoimmune myocarditis by suppressing local production of interleukin 17," *The Journal of Experimental Medicine* 203(8):2009-2019, 2006.
Raviprakash et al., "Inhibition of Dengue Virus by Novel, Modified Antisense Oligonucleotides," *Journal of Virology* 69(1):69-74, 1995. (9 pages).
Richard et al., "Cell-penetrating Peptides. A Reevaluation of the Mechanism of Cellular Uptake," *The Journal of Biological Chemistry* 278(1):585-590, Jan. 3, 2003.

(56) References Cited

OTHER PUBLICATIONS

Ricker et al., "c-myc antisense oligonucleotide treatment ameliorates murine ARPKD," *Kidney International* 61:S125-S131, 2002.
Roehl et al., "Poliovirus Infection Enhances the Formation of Two Ribonucleoprotein Complexes at the 3' End of Viral Negative-Strand RNA," *Journal of Virology* 69(5):2954-2961, 1995.
Roehl et al., "Processing of a Cellular Polypeptide by 3CD Proteinase is Required for Poliovirus Ribonucleoprotein Complex Formation," *Journal of Virology* 71(1):578-585, 1997.
Rothbard et al., "Arginine-Rich Molecular Transporters for Drug Delivery: Role of Backbone Spacing in Cellular Uptake," *J. Med. Chem.* 45:3612-3618, 2002.
Salomon et al., "Complexities of CD28/B7: CTLA-4 Costimulatory Pathways in Autoimmunity and Transplantation," *Annu. Rev. Immunol.* 19:225-252, 2001.
Samoylova et al., "Elucidation of Muscle-Binding Peptides by Phage Display Screening," *Muscle & Nerve* 22(4):460-466, Apr. 1999.
Sanchez et al., "Sequence analysis of the Ebola virus genome: organization, genetic elements, and comparison with the genome of Marburg virus," *Virus Research* 29:215-240, 1993.
Sankar et al., "Antisense oligonucleotide inhibition of encephalomyocarditis virus RNA translation," *Eur. J. Biochem.* 184:39-45, 1989.
Sazani et al., "Systemically delivered antisense oligomers upregulate gene expression in mouse tissues," *Nature Biotechnology* 20:1228-1233, 2002.
Shafer et al., "Biological Aspects of DNA/RNA Quadruplexes," *Biopolymers* 56(3):209-227, 2001.
Siprashvili et al., "Gene Transfer via Reversible Plasmid Condensation with Cysteine-Flanked, Internally Spaced Arginine-Rich Peptides," *Human Gene Therapy* 14:1225-1233, 2003.
Smith et al., "Antisense treatment of Caliciviridae: An emerging disease agent of animals and humans," *Current Opinion Molecular Therapeutics* 4(2):177-184, 2002.
Smith et al., "Calicivirus Emergence from Ocean Reservoirs: Zoonotic And Interspecies Movements," *Emerging Infectious Diseases* 4(1):13-20, 1998.
Smith et al., "Secondary structure and hybridization accessibility of the hepatitis C virus negative strand RNA 5'-terminus," *Journal of Viral Hepatitis* 11:115-123, 2004.
Spence et al., "Generation of cellular immunity to lymphocytic choriomeningitis virus is independent of CD1d1 expression," *Immunology* 104:168-174, 2001.
Stein et al., "A Specificity Comparison of Four Antisense Types: Morpholino, 2'-O-methyl RNA, DNA, and Phosphorothioate DNA," *Antisense & Nucleic Acid Drug Development* 7:151-157, 1997.
Stein et al., "Antisense Antiviral Agent and Method for Treating ssRNA Viral Infection," Office Action dated Feb. 17, 2010, for U.S. Appl. No. 11/431,968, 19 pages.
Stein et al., "Inhibition of Vesivirus Infections in Mammalian Tissue Culture with Antisense Morpholino Oligomers," *Antisense & Nucleic Acid Drug Development* 11:317-325, 2001.
Summerton et al., "Morpholino and Phosphorothioate Antisense Oligomers Compared in Cell-Free and In-Cell Systems," *Antisense & Nucleic Acid Drug Development* 7:63-70, 1997.
Summerton et al., "Morpholino Antisense Oligomers: Design, Preparation, and Properties," *Antisense & Nucleic Acid Drug Development* 7:187-195, 1997.
Summerton, "Morpholino antisense oligomers: the case for an RNase H-independent structural type," *Biochimica et Biophysica Acta* 1489:141-158, 1999.
Summerton, "Morpholinos and PNAs Compared," Ch. 6, pp. 89-113, In; *Peptide Nucleic Acids, Morpholinos, and Related Antisense Biomolecules*, Eds.: Janson et al. Landes Publishers, Austin, Texas, 2006.
Summerton, *Peptide Nucleic Acids, Morpholinos, and Related Antisense Biomolecules*, Landes Bioscience/Eurekah.com and Kluwer Academic/Plenum Publishers, ed. C.G Janson and M.J. During, 2006, Chapter 6, "Morpholinos and PNAs Compared," pp. 89-113.
Tan et al., "Peptide Nucleic Acid Antisense Oligomer as a Therapeutic Strategy against Bacterial Infection: Proof of Principle Using Mouse Intraperitoneal Infection," *Antimicrobial Agents and Chemotherapy* 49(8):3203-3207, 2005.
Taylor et al., "Antisense oligonucleotides: a systematic high-throughput approach to target validation and gene function determination," *DDT* 4(12):562-567, 1999.
Thiel et al., "Infectious RNA transcribed in vitro from a cDNA copy of the human coronavirus genome cloned in vaccinia virus," *Journal of General Virology* 82:1273-1281, 2001.
Tilley et al., "Gene-Specific Effects of Antisense Phosphorodiamidate Morpholino Oligomer-Peptide Conjugates on *Escherichia coli* and *Salmonella enteric* Serovar Typhimurium in Pure Culture and in Tissue Culture," *Antimicrobial Agents and Chemotherapy* 50(8):2789-2796, 2006.
Tilley et al., "Antisense peptide-phosphorodiamidate morpholino oligomer conjugate: dose-response in mice infected with *Escherichia coli*," *Journal of Antimicrobial Chemotherapy* 59:66-73, 2007.
Toulme et al., "Targeting RNA structures by antisense oligonucleotides," *Biochimie* 78:663-673, 1996.
Uhlmann et al., "Antisense Oligonucleotides: A New Therapeutic Principle," *Chemical Reviews* 90(4):544-584, 1990. (42 pages).
Van der Merwe et al., "Molecular Interactions Mediating T Cell Antigen Recognition," *Annu. Rev. Immunol.* 21:659-684, 2003.
Van Helvoort et al., "Chloramphenicol Causes Fusion of Separated Nucleoids in *Escherichia coli* K-12 Cells and Filaments," J Bacteriology 178(14): 4289-4293, Jul. 1996.
Vanin et al., "Synthesis and Application of Cleavable Photoactivable Heterobifunctional reagents," *Biochemistry* 20:6754-6760, 1981.
Vijayakrishnan et al., "An Autoimmune Disease-Associated CTLA-4 Splice Variant Lacking the B7 Binding Domain Signals Negatively in T Cells," *Immunity* 20(5):563-575, 2004.
Vives et al., "TAT Peptide Internalization: Seeking the Mechanism of Entry," *Current Protein and Peptide Science* 4:125-132, 2003.
Wages et al., "Affinity Purification of RNA: Sequence-Specific Capture by Nonionic Morpholino Probes," *BioTechniques* 23:1116-1121, 1997.
Wang et al., "Assessment of the utilization of the antisense RNA strategy to identify essential genes in heterologous bacteria," *FEMS Microbiology Letters* 220(2):171-176, 2003.
Wang et al., "Specific Inhibition of Coxsackievirus B3 Translation and Replication by Phosphorothioate Antisense Oligodeoxynucleotides," *Antimicrobial Agents Chemotherapy* 45(4):1043-1052, 2001.
Wang et al., "Synthesis of Antisense Phosphothioate Oligodeoxynucleotides of Dengue Fever Virus and their Anti-Viral Activity," *Progress of Biochemistry and Biophysics* 24(1): 4 pages, 1997. (20 pages).
Warfield et al., "Role of Natural Killer Cells in Innate Protection against Lethal Ebola Virus Infection," *The Journal of Experimental Medicine* 200(2):169-179, 2004.
Warfield et al., "Gene-Specific Countermeasures against Ebola Virus Based on Antisense Phosphorodiamidate Morpholino Oligomers," *PLoS Pathogens* 2(1):5-13, 2006.
Wasem et al., "Sensitizing antigen-specific CD8+ T cells for accelerated suicide causes immune incompetence," *The Journal of Clinical Investigation* 111(8):1191-1199, 2003.
Wei et al., "Human immunodeficiency virus type-1 reverse transcription can be inhibited in vitro by oligonucleotides that target both natural and synthetic tRNA primers," *Nucleic Acids Research* 28(16):3065-3074, 2000.
Advisory Action, dated Oct. 28, 2010, for U.S. Appl. No. 11/801,885,Weller et al., "Oligonucleotide Analogs Having Cationic Intersubunit Linkages," 6 pages.
Office Action, dated Aug. 18, 2010, for U.S. Appl. No. 11/801,885,Weller et al., "Oligonucleotide Analogs Having Cationic Intersubunit Linkages," 6 pages.
Wender et al., "Oligocarbamate Molecular Transporters: Design, Synthesis, and Biological Evaluation of a New Class of Transporters for Drug Delivery," *J. Am. Chem. Soc.* 124:13382-13383, 2002.
Wender et al., "The design, synthesis, and evaluation of molecules that enable or enhance cellular uptake: Peptoid molecular transporters," *PNAS* 97(24):13003-13008, 2000.

(56) References Cited

OTHER PUBLICATIONS

Wherry et al., "Viral Persistence Alters CD8 T-Cell Immunodominance and Tissue Distribution and Results in Distinct Stages of Functional Impairment," *Journal of Virology* 77(8):4911-4927, 2003.
Wiersinga, "Beyond Antibiotics: New Horizons in Treating *Burkholderia* Species Infections," *The Journal of Infectious Diseases* 201(12): 000-000, 2010. (2 pages).
Williams et al., "Cationic lipids reduce time and dose of c-myc antisense oligodeoxynucleotides required to specifically inhibit Burkitt's lymphoma cell growth," *Leukemia* 10:1980-1989, 1996.
Wilson et al., "Naturally Occurring Dicistronic Cricket Paralysis Virus RNA Is Regulated by Two Internal Ribosome Entry Sites," *Molecular and Cellular Biology* 20(14):4990-4999, 2000.
Wilton et al., "Antisense Oligonucleotide-induced Exon Skipping Across the Human Dystrophin Gene Transcript," *Molecular Therapy* 15(7):1288-1296, Jul. 2007.
Wright et al., "The Human IL-17F/IL-17A Heterodimeric Cytokine Signals through the IL-17RA/IL-17RC Receptor Complex," *The Journal of Immunology* 181:2799-2805, 2008 (8 pages).
Wu et al., "Specific Inhibition of Hepatitis B Viral Gene Expression in Vitro by Targeted Antisense Oligonucleotides," *The Journal of Biological Chemistry* 267(18):12436-12439, 1992.
Wu et al., "Cell-penetrating peptides as transporters for morpholino oligomers: effects of amino acid composition on intracellular delivery and cytotoxicity," *Nucleic Acids Research* 35(15):5182-5191, Aug. 2007.
Wu et al., "Receptor-mediated in Vitro Gene Transformation by a Soluble DNA Carrier System," *The Journal of Biological Chemistry* 262(10):4429-4432, 1987.
Xu et al., "Viral haemorrhagic disease of rabbits in the People's Republic of China: epidemiology and virus characterisation," *Rev. sci. tech. Off int. Epiz.* 10(2):393-408, 1991.
Yakubov et al., "Mechanism of oligonucleotide uptake by cells: Involvement of specific receptors?" *Proc. Natl. Acad. Sci. USA* 86:6454-6458, 1989.

Yauch et al., "Mouse models of dengue virus infection and disease," *Antiviral Research* 80:87-93, 2008.
Yin et al., "Effective Exon Skipping and Restoration of Dystrophin Expression by Peptide Nucleic Acid Antisense Oligonucleotides in mdx Mice," *Molecular Therapy* 16(1):38-45, Jan. 2008.
Yoo et al., "PAMAM Dendrimers as Delivery Agents for Antisense Oligonucleotides," *Pharmaceutical Research* 16(12):1799-1804, 1999.
Youngblood et al., "Stability of Cell-Penetrating Peptide—Morpholino Oligomer Conjugates in Human Serum and in Cells," *Bioconjugate Chem.* 18:50-60, 2007.
Zhang et al., "Antisense Oligonucleotide Inhibition of Hepatitis C Virus (HCV) Gene Expression in Livers of Mice Infected with an HCV-Vaccinia Virus Recombinant," *Antimicrobial Agents and Chemotherapy* 43(2):347-353, 1999.
Zhang et al., "RNA interference in mammalian cells by siRNAs modified with morpholino nucleoside analogues," *Bioorganic & Medicinal Chemistry* 17:2441-2446, 2009.
Zhang et al., "Construction of a novel chimera consisting of a chelator-containing Tat peptide conjugated to a morpholino antisense oligomers for technetium-99m labeling and accelerating cellular kinetics," *Nuclear Medicine and Biology* 33:263-269, 2006.
Zhang et al., "Polar Allele Duplication for Transcriptional Analysis of Consecutive Essential Genes: Application to a Cluster of *Escherichia coli* Fatty Acid Biosynthetic Genes," *Journal of Bacteriology* 178(12): 3614-3620, 1996.
Zhou et al., "IL-17A versus IL-17F induced intracellular signal transduction pathways and modulation by IL-17RA and IL-17RC RNA interference in AGS gastric adenocarcinoma cells," *Cytokine* 38:157-164, 2007.
Zollinger et al., "Meningococcal vaccines—present and future," *Transactions of Royal Soc of Tropical Medicine and Hygiene* 85(Supp. 1):37-43, 1991.
Zubin et al., "Oligonucleotide-peptide conjugates as potential antisense agents," *FEBS Letters* 456:59-62, 1999.
Zuker, "Mfold web server for nucleic acid folding and hybridization prediction," *Nucleic Acids Research* 31(13):3406-3415, 2003.

\* cited by examiner

SEQUENCE LISTING

<160> NUMBER OF SEQ ID NOS: 12

<210> SEQ ID NO 1
<211> LENGTH: 18
<212> TYPE: DNA
<213> ORGANISM: Artificial Sequence
<220> FEATURE:
<223> OTHER INFORMATION: A PMO designed to restore correct splicing in
      the enhanced green fluorescent protein (EGFP) gene

<400> SEQUENCE: 1
gctattacct taacccag                                                  18

<210> SEQ ID NO 2
<211> LENGTH: 18
<212> TYPE: DNA
<213> ORGANISM: Artificial Sequence
<220> FEATURE:
<223> OTHER INFORMATION: Synthetic oligomer sequence
<220> FEATURE:
<221> NAME/KEY: modified_base
<222> LOCATION: (1)...(1)
<223> OTHER INFORMATION: ethylene glycol trimer

<400> SEQUENCE: 2
gctattacct taacccag                                                  18

<210> SEQ ID NO 3
<211> LENGTH: 18
<212> TYPE: DNA
<213> ORGANISM: Artificial Sequence
<220> FEATURE:
<223> OTHER INFORMATION: Synthetic oligomer sequence
<220> FEATURE:
<221> NAME/KEY: modified_base
<222> LOCATION: (1)...(1)
<223> OTHER INFORMATION: Guanidine
<220> FEATURE:
<221> NAME/KEY: modified_base
<222> LOCATION: (2)...(2)
<223> OTHER INFORMATION: modified intersubunit linkage G-pip
<220> FEATURE:
<221> NAME/KEY: modified_base
<222> LOCATION: (5)...(5)
<223> OTHER INFORMATION: modified intersubunit linkage G-pip
<220> FEATURE:
<221> NAME/KEY: modified_base
<222> LOCATION: (10)...(10)
<223> OTHER INFORMATION: modified intersubunit linkage G-pip
<220> FEATURE:
<221> NAME/KEY: modified_base
<222> LOCATION: (18)...(18)
<223> OTHER INFORMATION: Trityl

<400> SEQUENCE: 3
gctattacct taacccag                                                  18

<210> SEQ ID NO 4
<211> LENGTH: 18
<212> TYPE: DNA
<213> ORGANISM: Artificial Sequence
<220> FEATURE:
<223> OTHER INFORMATION: Synthetic oligomer sequence
<220> FEATURE:
<221> NAME/KEY: modified_base
<222> LOCATION: (1)...(1)
<223> OTHER INFORMATION: ethylene glycol trimer
<220> FEATURE:
<221> NAME/KEY: modified_base
<222> LOCATION: (2)...(2)
<223> OTHER INFORMATION: modified intersubunit linkage map
<220> FEATURE:

-continued

```
<221> NAME/KEY: modified_base
<222> LOCATION: (4)...(4)
<223> OTHER INFORMATION: modified intersubunit linkage map
<220> FEATURE:
<221> NAME/KEY: modified_base
<222> LOCATION: (5)...(5)
<223> OTHER INFORMATION: modified intersubunit linkage map
<220> FEATURE:
<221> NAME/KEY: misc_structure
<222> LOCATION: (10)...(10)
<223> OTHER INFORMATION: modified intersubunit linkage map

<400> SEQUENCE: 4
gctattacct taacccag                                                18

<210> SEQ ID NO 5
<211> LENGTH: 18
<212> TYPE: DNA
<213> ORGANISM: Artificial Sequence
<220> FEATURE:
<223> OTHER INFORMATION: Synthetic oligomer sequence
<220> FEATURE:
<221> NAME/KEY: modified_base
<222> LOCATION: (1)...(1)
<223> OTHER INFORMATION: ethylene glycol trimer
<220> FEATURE:
<221> NAME/KEY: modified_base
<222> LOCATION: (2)...(2)
<223> OTHER INFORMATION: modified intersubunit linkage map
<220> FEATURE:
<221> NAME/KEY: modified_base
<222> LOCATION: (4)...(4)
<223> OTHER INFORMATION: modified intersubunit linkage map
<220> FEATURE:
<221> NAME/KEY: modified_base
<222> LOCATION: (5)...(5)
<223> OTHER INFORMATION: modified intersubunit linkage map
<220> FEATURE:
<221> NAME/KEY: modified_base
<222> LOCATION: (9)...(9)
<223> OTHER INFORMATION: modified intersubunit linkage map
<220> FEATURE:
<221> NAME/KEY: modified_base
<222> LOCATION: (10)...(10)
<223> OTHER INFORMATION: modified intersubunit linkage map

<400> SEQUENCE: 5
gctattacct taacccag                                                18

<210> SEQ ID NO 6
<211> LENGTH: 18
<212> TYPE: DNA
<213> ORGANISM: Artificial Sequence
<220> FEATURE:
<223> OTHER INFORMATION: Synthetic oligomer sequence
<220> FEATURE:
<221> NAME/KEY: modified_base
<222> LOCATION: (1)...(1)
<223> OTHER INFORMATION: modified intersubunit linkage morph and
      ethylene glycol trimer
<220> FEATURE:
<221> NAME/KEY: modified_base
<222> LOCATION: (2)...(2)
<223> OTHER INFORMATION: modified intersubunit linkage morph
<220> FEATURE:
<221> NAME/KEY: modified_base
<222> LOCATION: (3)...(3)
<223> OTHER INFORMATION: modified intersubunit linkage morph
<220> FEATURE:
<221> NAME/KEY: modified_base
<222> LOCATION: (4)...(4)
<223> OTHER INFORMATION: modified intersubunit linkage morph
<220> FEATURE:
<221> NAME/KEY: modified_base
<222> LOCATION: (5)...(5)
```

<223> OTHER INFORMATION: modified intersubunit linkage morph
<220> FEATURE:
<221> NAME/KEY: modified_base
<222> LOCATION: (6)...(6)
<223> OTHER INFORMATION: modified intersubunit linkage morph
<220> FEATURE:
<221> NAME/KEY: modified_base
<222> LOCATION: (7)...(7)
<223> OTHER INFORMATION: modified intersubunit linkage morph
<220> FEATURE:
<221> NAME/KEY: modified_base
<222> LOCATION: (8)...(8)
<223> OTHER INFORMATION: modified intersubunit linkage morph
<220> FEATURE:
<221> NAME/KEY: modified_base
<222> LOCATION: (9)...(9)
<223> OTHER INFORMATION: modified intersubunit linkage morph
<220> FEATURE:
<221> NAME/KEY: modified_base
<222> LOCATION: (10)...(10)
<223> OTHER INFORMATION: modified intersubunit linkage morph
<220> FEATURE:
<221> NAME/KEY: modified_base
<222> LOCATION: (11)...(11)
<223> OTHER INFORMATION: modified intersubunit linkage morph
<220> FEATURE:
<221> NAME/KEY: modified_base
<222> LOCATION: (12)...(12)
<223> OTHER INFORMATION: modified intersubunit linkage morph
<220> FEATURE:
<221> NAME/KEY: modified_base
<222> LOCATION: (13)...(13)
<223> OTHER INFORMATION: modified intersubunit linkage morph
<220> FEATURE:
<221> NAME/KEY: modified_base
<222> LOCATION: (14)...(14)
<223> OTHER INFORMATION: modified intersubunit linkage morph
<220> FEATURE:
<221> NAME/KEY: modified_base
<222> LOCATION: (15)...(15)
<223> OTHER INFORMATION: modified intersubunit linkage morph
<220> FEATURE:
<221> NAME/KEY: modified_base
<222> LOCATION: (16)...(16)
<223> OTHER INFORMATION: modified intersubunit linkage morph
<220> FEATURE:
<221> NAME/KEY: modified_base
<222> LOCATION: (17)...(17)
<223> OTHER INFORMATION: modified intersubunit linkage morph

<400> SEQUENCE: 6
gctattacct taacccag                                           18

<210> SEQ ID NO 7
<211> LENGTH: 18
<212> TYPE: DNA
<213> ORGANISM: Artificial Sequence
<220> FEATURE:
<223> OTHER INFORMATION: Synthetic oligomer sequence
<220> FEATURE:
<221> NAME/KEY: modified_base
<222> LOCATION: (1)...(1)
<223> OTHER INFORMATION: ethylene glycol trimer
<220> FEATURE:
<221> NAME/KEY: modified_base
<222> LOCATION: (2)...(2)
<223> OTHER INFORMATION: modified intersubunit linkage MG-pip
<220> FEATURE:
<221> NAME/KEY: modified_base
<222> LOCATION: (4)...(4)
<223> OTHER INFORMATION: modified intersubunit linkage MG-pip
<220> FEATURE:
<221> NAME/KEY: modified_base
<222> LOCATION: (5)...(5)
<223> OTHER INFORMATION: modified intersubunit linkage MG-pip
<220> FEATURE:
<221> NAME/KEY: modified_base

```
<222> LOCATION: (10)...(10)
<223> OTHER INFORMATION: modified intersubunit linkage MG-pip
<220> FEATURE:
<221> NAME/KEY: modified_base
<222> LOCATION: (18)...(18)
<223> OTHER INFORMATION: (NH)NH2

<400> SEQUENCE: 7
gctattacct taacccag                                                    18

<210> SEQ ID NO 8
<211> LENGTH: 18
<212> TYPE: DNA
<213> ORGANISM: Artificial Sequence
<220> FEATURE:
<223> OTHER INFORMATION: Synthetic oligomer sequence
<220> FEATURE:
<221> NAME/KEY: modified_base
<222> LOCATION: (1)...(1)
<223> OTHER INFORMATION: ethylene glycol trimer
<220> FEATURE:
<221> NAME/KEY: modified_base
<222> LOCATION: (2)...(2)
<223> OTHER INFORMATION: modified intersubunit linkage MG-pip
<220> FEATURE:
<221> NAME/KEY: modified_base
<222> LOCATION: (4)...(4)
<223> OTHER INFORMATION: modified intersubunit linkage MG-pip
<220> FEATURE:
<221> NAME/KEY: modified_base
<222> LOCATION: (5)...(5)
<223> OTHER INFORMATION: modified intersubunit linkage MG-pip
<220> FEATURE:
<221> NAME/KEY: modified_base
<222> LOCATION: (9)...(9)
<223> OTHER INFORMATION: modified intersubunit linkage MG-pip
<220> FEATURE:
<221> NAME/KEY: modified_base
<222> LOCATION: (10)...(10)
<223> OTHER INFORMATION: modified intersubunit linkage MG-pip
<220> FEATURE:
<221> NAME/KEY: modified_base
<222> LOCATION: (18)...(18)
<223> OTHER INFORMATION: (NH)NH2

<400> SEQUENCE: 8
gctattacct taacccag                                                    18

<210> SEQ ID NO 9
<211> LENGTH: 18
<212> TYPE: DNA
<213> ORGANISM: Artificial Sequence
<220> FEATURE:
<223> OTHER INFORMATION: Synthetic oligomer sequence
<220> FEATURE:
<221> NAME/KEY: modified_base
<222> LOCATION: (1)...(1)
<223> OTHER INFORMATION: ethylene glycol trimer
<220> FEATURE:
<221> NAME/KEY: modified_base
<222> LOCATION: (18)...(18)
<223> OTHER INFORMATION: (Arg aminohexanoic acid Arg Arg beta-alanine
      Arg Arg aminohexanoic acid Arg Arg beta-alanine Arg
      aminohexanoic acid beta alanine

<400> SEQUENCE: 9
gctattacct taacccag                                                    18

<210> SEQ ID NO 10
<211> LENGTH: 18
<212> TYPE: DNA
<213> ORGANISM: Artificial Sequence
<220> FEATURE:
```

```
<223> OTHER INFORMATION: Synthetic oligomer sequence
<220> FEATURE:
<221> NAME/KEY: modified_base
<222> LOCATION: (1)...(1)
<223> OTHER INFORMATION: ethylene glycol trimer
<220> FEATURE:
<221> NAME/KEY: modified_base
<222> LOCATION: (18)...(18)
<223> OTHER INFORMATION: Arg Arg Arg Arg Arg Arg Gly

<400> SEQUENCE: 10
gctattacct taacccag                                               18

<210> SEQ ID NO 11
<211> LENGTH: 18
<212> TYPE: DNA
<213> ORGANISM: Artificial Sequence
<220> FEATURE:
<223> OTHER INFORMATION: Synthetic oligomer sequence
<220> FEATURE:
<221> NAME/KEY: modified_base
<222> LOCATION: (1)...(1)
<223> OTHER INFORMATION: ethylene glycol trimer
<220> FEATURE:
<221> NAME/KEY: modified_base
<222> LOCATION: (2)...(2)
<223> OTHER INFORMATION: modified intersubunit linkage guanidinyl
<220> FEATURE:
<221> NAME/KEY: modified_base
<222> LOCATION: (5)...(5)
<223> OTHER INFORMATION: modified intersubunit linkage guanidinyl
<220> FEATURE:
<221> NAME/KEY: modified_base
<222> LOCATION: (10)...(10)
<223> OTHER INFORMATION: modified intersubunit linkage guanidinyl
<220> FEATURE:
<221> NAME/KEY: modified_base
<222> LOCATION: (18)...(18)
<223> OTHER INFORMATION: Guanidinyl

<400> SEQUENCE: 11
gctattacct taacccag                                               18

<210> SEQ ID NO 12
<211> LENGTH: 18
<212> TYPE: DNA
<213> ORGANISM: Artificial Sequence
<220> FEATURE:
<223> OTHER INFORMATION: Synthetic oligomer sequence
<220> FEATURE:
<221> NAME/KEY: modified_base
<222> LOCATION: (1)...(1)
<223> OTHER INFORMATION: ethylene glycol trimer
<220> FEATURE:
<221> NAME/KEY: modified_base
<222> LOCATION: (2)...(2)
<223> OTHER INFORMATION: modified intersubunit linkage apn
<220> FEATURE:
<221> NAME/KEY: modified_base
<222> LOCATION: (5)...(5)
<223> OTHER INFORMATION: modified intersubunit linkage apn
<220> FEATURE:
<221> NAME/KEY: modified_base
<222> LOCATION: (10)...(10)
<223> OTHER INFORMATION: modified intersubunit linkage apn

<400> SEQUENCE: 12
gctattacct taacccag                                               18
```

METHODS AND COMPOUNDS FOR TREATMENT OF LYMPHOCYTE-RELATED DISEASES AND CONDITIONS

STATEMENT REGARDING SEQUENCE LISTING

The Sequence Listing associated with this application is provided in text format in lieu of a paper copy, and is hereby incorporated by reference into the specification. The name of the text file containing the Sequence Listing is 120178_50001WO_SEQUENCE_LISTING.txt. The text file is 8.2 KB, was created on Jun. 2, 2016, and is being submitted electronically via EFS-Web.

BACKGROUND

Technical Field

The present invention is generally related to oligonucleotide compounds (oligomers) and methods for their use as antisense compounds, and more particularly to methods for use of the oligonucleotide compounds for treatment of lymphocyte-related diseases and conditions.

Description of the Related Art

Antisense oligonucleotides are useful tools for inhibiting gene expression and are the subject of ongoing investigation as therapeutic agents. Lymphoid cells, including T lymphocytes and B lymphocytes, are important target cells for therapeutic antisense strategies. Lymphocytes are white blood cells that largely mediate the adaptive immune response. Lymphocytes include natural killer (NK) cells, T cells, and B cells. T cells and B cells are involved in cell-mediated immunity and humoral immunity, respectively, through their recognition of "non-self" antigens via cell surface receptors. The antigen receptor of B cells is a membrane bound form of the immunoglobulin that they will secret upon activation. Upon activation (i.e., binding of the antigen to the B cell receptor), the B cell differentiates into plasma cells that secrete immunoglobulins. The antigen receptor of T cells is a membrane bound heterodimeric receptor associated with the proteins of the CD3 complex. Most T lymphocytes have $\alpha{:}\beta$ heterodimeric receptors, but some T cells have $\gamma{:}\delta$ receptors.

Two simultaneous signals are required to activate a T lymphocyte. One signal is provided by a peptide bound to an WIC protein on the surface of an antigen presenting cell (APC). The peptide-WIC complex signals through the T cell receptor and its associated proteins. The second signal is provided by co-stimulatory molecules on the APC (e.g., CD80 and CD86), which are recognized by a co-stimulatory receptor (e.g., CD28) on the T cell surface. The combination of the two signals stimulates the T cell to proliferate and begin to differentiate into an effector T cell (e.g., cytotoxic $CD8^+$ T cell, $T_H1$ cell, $T_H2$ cell). Cytotoxic T cells kill infected target cells through the release of lytic granules into antigen-bearing target cells. $T_H1$ cells activate microbicidal properties of infected macrophages and induce B cells to produce opsonizing IgG antibodies. $T_H2$ cells activate naïve B cells to secrete IgM and induce production of other antibody isotypes. Regulatory T cells (Tregs) are a subpopulation of T cells involved in maintaining tolerance to self-antigens. Treg function or dysfunction may be an important factor in numerous pathological settings, including autoimmunity, allergy, infection, tumor immunity, organ transplantation, and fetal-maternal tolerance.

T cells are frequent therapeutic targets for inhibiting chronic inflammation or cytotoxicity associated with autoimmune diseases. For example, defective apoptosis of autoreactive T cells is implicated in the pathogenesis of multiple sclerosis. Antisense oligonucleotides for an X-linked inhibitor of apoptosis (XIAP) was found to increase susceptibility of T cells to activation-induced apoptosis in vitro and alleviated experimental autoimmune encephalomyelitis and prevented relapses in mice (Zehntner et al., 2007, J. Immunol. 179:7553-7560). In another example, migration of T lymphocytes into the intestinal mucosa plays a crucial role in the pathogenesis of inflammatory bowel disease (IBD) (e.g., Crohn's disease or ulcerative colitis). Antisense inhibition of Smad7, an inhibitor of TGF-$\beta$1 signaling that is overexpressed in inflammatory bowel disease mucosa and purified mucosal T cells, enabled IBD cell samples to respond to TGF-$\beta$1 and downregulated proinflammatory cytokines (U.S. Pat. No. 7,700,757; Monteleone et al., 2001, J. Clin. Invest. 108:601-609). In yet another example, synovial T cells may play a crucial role in rheumatoid arthritis induction and promotion, in part due to the production of the proinflammatory cytokine IL-17. Antisense targeting of the transcription factor STAT4 in T lymphocytes suppressed clinical and histopathological signs of collagen-induced arthritis in mice (Hildner et al., 2007, J. Immunol. 178:3427-3436).

The rejection of allogeneic transplants is largely mediated by T cells. Antisense oligonucleotides have been used to inhibit granzyme expression in cytotoxic T lymphocytes, which is associated with tissue destruction in transplantation models (Bailey et al., 2004, Eur. J. Immunol., 27:2302-2309).

HIV-infected T lymphocytes, particularly T helper lymphocytes, or $CD4^+$ T lymphocytes, are targets for antisense strategies against HIV (Lisziewicz et al., 1994, Proc. Natl. Acad. Sci. USA 91:7942-7946; Zhang et al., 1995, Clin. Pharmacol. Ther. 58:44-53; Elmen et al., 2004, FEBS Lett. 578:285-90; Jakobsen et al., 2007, Retrovirology 4:29-41).

Lymphoid cells are also targeted by antisense oligonucleotides for antitumor therapy. By way of example, human T-cell leukemia virus type 1 (HTLV-1) infection is known to cause adult T cell leukemia. Inhibition of syncytium formation in T-cells was observed in vitro with antisense oligonucleotides targeting human T-cell leukemia virus type 1 HTLV-1 tax gene (Maeda et al., 1997, Leukemia 11:42-44). In another example, antisense-mediated inhibition of the protooncogene c-myb inhibited DNA synthesis in T-leukemia cells of most patients (Venturelli et al., 1990 Cancer Res. 50:7371-7375). In yet another example, depletion of regulatory T cells with FOXP3-specific antisense oligonucleotides is being investigated as a way to enhance effector T cell response to tumors (Morse et al., 2012, Cancer Gene Ther. 19:30-37).

Functional efficacy of such antisense oligonucleotide based therapy is limited by insufficient cellular uptake of the oligonucleotide. Exogenous oligonucleotides are primarily taken up through fluid phase endocytosis at oligonucleotide concentrations greater than 1 µM and endocytosis mediated by a receptor-like protein for lower concentrations (Beltinger et al., 1995, J. Clin. Invest. 95:1814-1823). Primary cells are known to incorporate oligonucleotides less efficiently than cell lines (Marti et al., 1992, Antisense Res. Dev. 2:27-39). Furthermore, oligonucleotide uptake is heterogenous among different cell types. Among normal peripheral blood and bone marrow cells, myeloid cells and B cells preferably took up more oligonucleotides than T cells (Zhao et al., 1996, Blood 88:1788-1795). Other studies also showed preferential uptake of oligonucleotides by monocytes and B cells and very low uptake by T cells (Hartmann et al., 1998, J. Pharmacol. Exp. Ther. 285:920-928; Kronenwett et al., 1998, Blood 91:852-862). In fact, Hartmann et al. demonstrated that only 2% of T cells spontaneously incorporated FITC-labeled phosphorothioate oligonucleotides as measured by fluorescence intensity. Mitogen activation may increase oligonucleotide uptake (Kreig et al., 1991, Antisense Res. Dev. 1:161-171; Iversen et al., 1992, Antisense Res. Dev. 2:223-233). Cationic lipids have been used to enhance oligonucleotide uptake into T cells with variable results (Hartmann et al., supra; Kronenwett et al., supra).

T cells are important targets for inhibition by antisense oligonucleotides in the treatment of inflammatory, infectious, and neoplastic diseases. There is a need for alternative compositions and methods for improving uptake of antisense oligonucleotides into T cells. The present disclosure meets this need and further provides other related advantages.

BRIEF SUMMARY

Methods described herein are useful for treatment of various lymphocyte (e.g., T-cell) mediated diseases or conditions. While not wishing to be bound to any particular theory, the present applicants believe the presence of certain functional groups, such as guanidinyl, alkylguanidinyl and/or alkylaminyl groups, in antisense oligonucleotides unexpectedly enhances delivery of the antisense oligonucleotides to lymphocytes, such as T-cells. Accordingly, in one embodiment the present disclosure provides a method for treatment of a lymphocyte-related disease or condition, the method comprising administering an effective amount of an oligomer to a patient in need thereof, wherein the oligomer comprises a backbone having a sequence of morpholino ring structures joined by intersubunit linkages, the intersubunit linkages joining a 3'-end of one morpholino ring structure to a 5'-end of an adjacent morpholino ring structure, wherein each morpholino ring structure is bound to a base-pairing moiety, such that the oligomer can bind in a sequence-specific manner to a target nucleic acid, wherein at least one of the intersubunit linkages has the following structure (I):

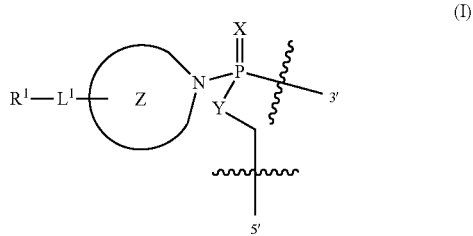

or a pharmaceutically acceptable salt, tautomer or stereoisomer thereof, wherein $R^1$, $L^1$, X, Y and Z are as defined herein.

In certain embodiments, the method is for treatment of a T-cell related disease or condition, the method comprising contacting activated T-cells with the above described oligomer.

These and other aspects of the invention will be apparent upon reference to the following detailed description. To this end, various references are set forth herein which describe in more detail certain background information, procedures, compounds and/or compositions, and are each hereby incorporated by reference in their entirety.

BRIEF DESCRIPTION OF THE DRAWINGS

In the figures, identical reference numbers identify similar elements. The sizes and relative positions of elements in the figures are not necessarily drawn to scale and some of these elements are arbitrarily enlarged and positioned to improve figure legibility. Further, the particular shapes of the elements as drawn are not intended to convey any information regarding the actual shape of the particular elements, and have been solely selected for ease of recognition in the figures.

DETAILED DESCRIPTION

Figure 1:
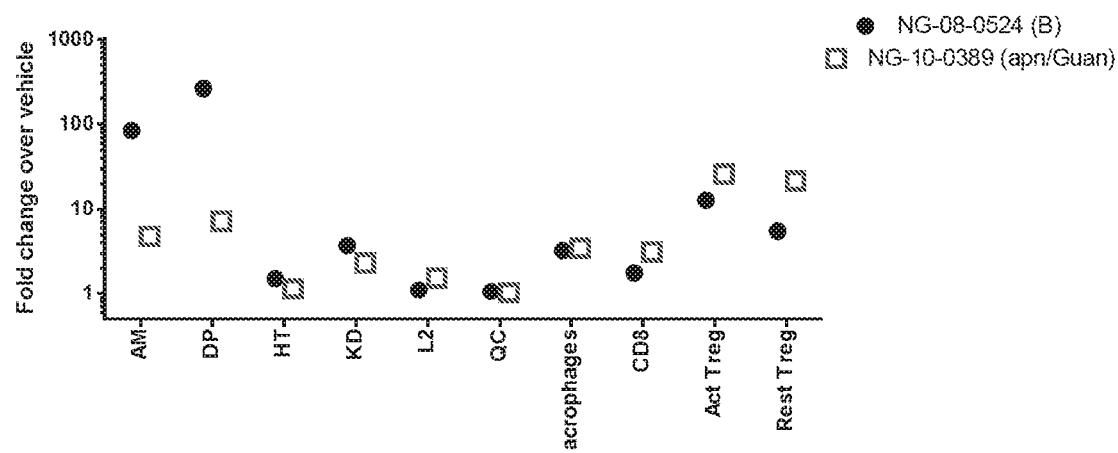
FIG. 1 shows tissue distribution data for a guanidinyl modified oligomer relative to a peptide conjugated oligomer. AM—abdominal muscle; DP—diaphragm; HT—heart; KD—kidney; L2—liver lobe 2; QC—quadriceps; CD8—CD8 T-cells; Act T reg—activated T-regulatory cells; Rest Treg—resting T regulatory cells.

In the following description, certain specific details are set forth in order to provide a thorough understanding of various embodiments. However, one skilled in the art will understand that the invention may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed invention.

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. Also, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The terms below, as used herein, have the following meanings, unless indicated otherwise:

"Amino" refers to the —NH$_2$ radical.

"Cyano" or "nitrile" refers to the —CN radical.

"Hydroxy" or "hydroxyl" refers to the —OH radical.

"Imino" refers to the =NH substituent.

"Guanidinyl" refers to the —NHC(=NH)NH$_2$ substituent.

"Nitro" refers to the —NO$_2$ radical.

"Oxo" refers to the =O substituent.

"Thioxo" refers to the =S substituent.

"Alkyl" refers to a straight or branched hydrocarbon chain radical which is saturated or unsaturated (i.e., contains one or more double and/or triple bonds), having from one to thirty carbon atoms, and which is attached to the rest of the molecule by a single bond. Alkyls comprising any number of carbon atoms from 1 to 30 are included. An alkyl comprising up to 30 carbon atoms is referred to as a $C_1$-$C_{30}$ alkyl, likewise, for example, an alkyl comprising up to 12 carbon atoms is a $C_1$-$C_{12}$ alkyl. Alkyls (and other moieties defined herein) comprising other numbers of carbon atoms are represented similarly. Alkyl groups include, but are not limited to, $C_1$-$C_{30}$ alkyl, $C_1$-$C_{20}$ alkyl, $C_1$-$C_{15}$ alkyl, $C_1$-$C_{10}$ alkyl, $C_1$-$C_8$ alkyl, $C_1$-$C_6$ alkyl, $C_1$-$C_4$ alkyl, $C_1$-$C_3$ alkyl, $C_1$-$C_2$ alkyl, $C_2$-$C_8$ alkyl, $C_3$-$C_8$ alkyl and $C_4$-$C_8$ alkyl. Representative alkyl groups include, but are not limited to, methyl, ethyl, n-propyl, 1-methylethyl (iso-propyl), n-butyl, s-butyl, n-pentyl, 1,1-dimethylethyl (t-butyl), 3-methylhexyl, 2-methylhexyl, ethenyl, prop-1-enyl, but-1-enyl, pent-1-enyl, penta-1,4-dienyl, ethynyl, propynyl, but-2-ynyl, but-3-ynyl, pentynyl, hexynyl, and the like. Unless stated otherwise specifically in the specification, an alkyl group is optionally substituted as described below.

"Alkylguanidinyl" refers to a radical of the formula —NR$_a$C(=NR$_a$)N(R$_a$)$_2$ where each R$_a$ is, independently, H or an alkyl radical as defined above, provided at least one R$_a$ is an alkyl radical Unless stated otherwise specifically in the specification, an alkylguanidinyl group is optionally substituted as described below.

"Alkylene" or "alkylene chain" refers to a straight or branched divalent hydrocarbon chain linking the rest of the molecule to a radical group. Alkylenes may be saturated or unsaturated (i.e., contains one or more double and/or triple bonds). Representative alkylenes include, but are not limited to, $C_1$-$C_{12}$ alkylene, $C_1$-$C_8$ alkylene, $C_1$-$C_6$ alkylene, $C_1$-$C_4$ alkylene, $C_1$-$C_3$ alkylene, $C_1$-$C_2$ alkylene, $C_1$ alkylene. Representative alkylene groups include, but are not limited to, methylene, ethylene, propylene, n-butylene, ethenylene, propenylene, n-butenylene, propynylene, n-butynylene, and the like. The alkylene chain is attached to the rest of the molecule through a single or double bond and to the radical group through a single or double bond. The points of attachment of the alkylene chain to the rest of the molecule and to the radical group can be through one carbon or any two carbons within the chain. Unless stated otherwise specifically in the specification, an alkylene chain is optionally substituted as described below. For example, in certain embodiments the alkylene is substituted with oxo.

"Aminoalkylene" refers to an alkylene as defined above, wherein the hydrocarbon chain is interrupted by (i.e., includes) at least one nitrogen atom. The nitrogen atom(s) may be at any position in the hydrocarbon chain, including the terminal ends (i.e., the nitrogen atom may link the hydrocarbon chain to the rest of the molecule and/or to the radical group). Unless stated otherwise specifically in the specification, an aminoalkylene group is optionally substituted as described below.

"Oxyalkylene" refers to an alkylene as defined above, wherein the hydrocarbon chain is interrupted by (i.e., includes) at least one oxygen atom. The oxygen atom(s) may be at any position in the hydrocarbon chain, including the terminal ends (i.e., the oxygen atom may link the hydrocarbon chain to the rest of the molecule and/or to the radical group). Unless stated otherwise specifically in the specification, an oxyalkylene group is optionally substituted as described below.

"Thioalkylene" refers to an alkylene as defined above, wherein the hydrocarbon chain is interrupted by (i.e., includes) at least one sulfur atom. The sulfur atom(s) may be at any position in the hydrocarbon chain, including the terminal ends (i.e., the sulfur atom may link the hydrocarbon chain to the rest of the molecule and/or to the radical group). Unless stated otherwise specifically in the specification, a thioalkylene group is optionally substituted as described below.

"Alkylaminyl" refers to a radical of the formula —NHR$_a$ or —NR$_a$R$_a$ where each R$_a$ is, independently, an alkyl radical as defined above. Unless stated otherwise specifically in the specification, an alkylamino group is optionally substituted as described below.

"Fused" refers to any ring structure described herein which is fused to an existing ring structure. When the fused ring is a heterocyclyl ring or a heteroaryl ring, any carbon atom on the existing ring structure which becomes part of the fused heterocyclyl ring or the fused heteroaryl ring may be replaced with a nitrogen atom.

"Halo" or "halogen" refers to bromo, chloro, fluoro or iodo.

"Heterocyclyl", "heterocycle" or "heterocyclic ring" refers to a stable 3-to 24-membered non-aromatic ring radical comprising 2 to 23 carbon atoms and from one to 8 heteroatoms selected from the group consisting of nitrogen, oxygen, phosphorous and sulfur. Unless stated otherwise specifically in the specification, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl, 12-crown-4, 15-crown-5, 18-crown-6, 21-crown-7, aza-18-crown-6, diaza-18-crown-6, aza-21-crown-7, and diaza-21-crown-7. Unless stated otherwise specifically in the specification, a heterocyclyl group may be optionally substituted.

All the above groups may be either substituted or unsubstituted. The term "substituted" as used herein means any of the above groups (e.g., alkyl, alkylguanidinyl, alkylene, aminoalkylene, oxyalkylene, thioalkylene, alkylaminyl and/or heterocyclyl), may be further functionalized wherein at least one hydrogen atom is replaced by a bond to a non-hydrogen atom substituent. Unless stated specifically in the specification, a substituted group may include one or more substituents selected from: amino, oxo, —CO$_2$H, nitrile, nitro, —CONH$_2$, hydroxyl, imino, thio, alkyl, alkylene, alkoxy, alkoxyalkyl, alkylcarbonyl, alkyloxycarbonyl, aryl, aralkyl, arylcarbonyl, aryloxycarbonyl, aralkylcarbonyl, aralkyloxycarbonyl, aryloxy, cycloalkyl, cycloalkylalkyl, cycloalkylcarbonyl, cycloalkylalkylcarbonyl, cycloalkyloxycarbonyl, heterocyclyl, heteroaryl, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, triarylsilyl groups, perfluoroalkyl or perfluoroalkoxy, for example, trifluoromethyl or trifluoromethoxy. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —NR$_g$C(=O)NR$_g$R$_h$, —NR$_g$C(=O)OR$_h$, —NR$_g$ SO$_2$R$_h$, —OC(=O)NR$_g$R$_h$, —OR$_g$, —SR$_g$, —SOR$_g$, —SO$_2$R$_g$, —OSO$_2$R$_g$, —SO$_2$OR$_g$, =NSO$_2$R$_g$, and —SO$_2$NR$_g$R$_h$. "Substituted" also means any of the above groups in which one or more hydrogen atoms are replaced with —C(=O)R$_g$, —C(=O)OR$_g$, —CH$_2$SO$_2$R$_g$, —CH$_2$SO$_2$NR$_g$R$_h$, —SH, —SR$_g$ or —SSR$_g$. In the foregoing, R$_g$ and R$_h$ are the same or different and independently hydrogen, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl. In addition, each of the foregoing substituents may also be optionally substituted with one or more of the above substituents. Furthermore, any of the above groups may be substituted to include one or more internal oxygen or sulfur atoms. For example, an alkyl group may be substituted with one or more internal oxygen atoms to form an ether or polyether group. Similarly, an alkyl group may be substituted with one or more internal sulfur atoms to form a thioether, disulfide, etc.

The terms "antisense oligomer" or "antisense compound" are used interchangeably and refer to a sequence of subunits, each having a base carried on a backbone subunit composed of ribose or other pentose sugar or morpholino group, and where the backbone groups are linked by intersubunit linkages that allow the bases in the compound to hybridize to a target sequence in a nucleic acid (typically an RNA) by Watson-Crick base pairing, to form a nucleic acid:oligomer heteroduplex within the target sequence. The oligomer may have exact sequence complementarity to the target sequence or near complementarity. Such antisense oligomers are designed to block or inhibit translation of the mRNA containing the target sequence, and may be said to be "directed to" a sequence with which it hybridizes.

A "morpholino oligomer" or "PMO" refers to a polymeric molecule having a backbone which supports bases capable of hydrogen bonding to typical polynucleotides, wherein the polymer lacks a pentose sugar backbone moiety, and more specifically a ribose backbone linked by phosphodiester bonds which is typical of nucleotides and nucleosides, but instead contains a ring nitrogen with coupling through the ring nitrogen. An exemplary "morpholino" oligomer comprises morpholino subunit structures linked together by (thio)phosphoramidate or (thio)phosphorodiamidate linkages, joining the morpholino nitrogen of one subunit to the 5' exocyclic carbon of an adjacent subunit, each subunit comprising a purine or pyrimidine base-pairing moiety effective to bind, by base-specific hydrogen bonding, to a base in a polynucleotide. Morpholino oligomers (including antisense oligomers) are detailed, for example, in U.S. Pat. Nos. 5,698,685; 5,217,866; 5,142,047; 5,034,506; 5,166,315; 5,185,444; 5,521,063; 5,506,337 and pending U.S. patent application Ser. Nos. 12/271,036; 12/271,040; and PCT publication number WO/2009/064471 all of which are incorporated herein by reference in their entirety. Representative PMOs include PMOs wherein the intersubunit linkages are linkage (A1).

A "phosphoramidate" group comprises phosphorus having three attached oxygen atoms and one attached nitrogen atom, while a "phosphorodiamidate" group comprises phosphorus having two attached oxygen atoms and two attached nitrogen atoms. In the uncharged or the modified intersubunit linkages of the oligomers described herein and co-pending US Patent Application Nos. 61/349,783 and Ser. No. 11/801,885, one nitrogen is always pendant to the backbone chain. The second nitrogen, in a phosphorodiamidate linkage, is typically the ring nitrogen in a morpholino ring structure.

"Thiophosphoramidate" or "thiophosphorodiamidate" linkages are phosphoramidate or phosphorodiamidate linkages, respectively, wherein one oxygen atom, typically the oxygen pendant to the backbone, is replaced with sulfur.

"Intersubunit linkage" refers to the linkage connecting two morpholino subunits, for example structure (I).

"Charged", "uncharged", "cationic" and "anionic" as used herein refer to the predominant state of a chemical moiety at near-neutral pH, e.g., about 6 to 8. For example, the term may refer to the predominant state of the chemical moiety at physiological pH, that is, about 7.4.

"Lower alkyl" refers to an alkyl radical of one to six carbon atoms, as exemplified by methyl, ethyl, n-butyl, i-butyl, t-butyl, isoamyl, n-pentyl, and isopentyl. In certain embodiments, a "lower alkyl" group has one to four carbon atoms. In other embodiments a "lower alkyl" group has one to two carbon atoms; i.e. methyl or ethyl. Analogously, "lower alkenyl" refers to an alkenyl radical of two to six, preferably three or four, carbon atoms, as exemplified by allyl and butenyl.

A "non-interfering" substituent is one that does not adversely affect the ability of an antisense oligomer as described herein to bind to its intended target. Such substituents include small and/or relatively non-polar groups such as methyl, ethyl, methoxy, ethoxy, or fluoro.

An oligonucleotide or antisense oligomer "specifically hybridizes" to a target polynucleotide if the oligomer hybridizes to the target under physiological conditions, with a Tm greater than 37° C., greater than 45° C., preferably at least 50° C., and typically 60° C.-80° C. or higher. The "Tm" of an oligomer is the temperature at which 50% hybridizes to a complementary polynucleotide. Tm is determined under standard conditions in physiological saline, as described, for example, in Miyada et al., *Methods Enzymol.* 154:94-107 (1987). Such hybridization may occur with "near" or "substantial" complementary of the antisense oligomer to the target sequence, as well as with exact complementarity.

Polynucleotides are described as "complementary" to one another when hybridization occurs in an antiparallel configuration between two single-stranded polynucleotides. Complementarity (the degree that one polynucleotide is complementary with another) is quantifiable in terms of the proportion of bases in opposing strands that are expected to form hydrogen bonds with each other, according to generally accepted base-pairing rules.

A first sequence is an "antisense sequence" with respect to a second sequence if a polynucleotide whose sequence is the first sequence specifically binds to, or specifically hybridizes with, the second polynucleotide sequence under physiological conditions.

The term "targeting sequence" is the sequence in the oligonucleotide analog that is complementary (meaning, in addition, substantially complementary) to the target sequence in the RNA genome. The entire sequence, or only a portion, of the analog compound may be complementary to the target sequence. For example, in some embodiments an analog having 20 bases, only 12-14 may be targeting sequences. Typically, the targeting sequence is formed of contiguous bases in the analog, but may alternatively be formed of non-contiguous sequences that when placed together, e.g., from opposite ends of the analog, constitute sequence that spans the target sequence.

Target and targeting sequences are described as "complementary" to one another when hybridization occurs in an antiparallel configuration. A targeting sequence may have "near" or "substantial" complementarity to the target sequence and still function for the purpose of the presently described methods, that is, still be "complementary." Preferably, the oligonucleotide analog compounds employed in the presently described methods have at most one mismatch with the target sequence out of 10 nucleotides, and preferably at most one mismatch out of 20. Alternatively, the antisense oligomers employed have at least 90% sequence homology, and preferably at least 95% sequence homology, with the exemplary targeting sequences as designated herein. For purposes of complementary binding to an RNA target, and as discussed below, a guanine base may be complementary to either a cytosine or uracil RNA base.

A "heteroduplex" refers to a duplex between an oligonucleotide analog and the complementary portion of a target RNA. A "nuclease-resistant heteroduplex" refers to a heteroduplex formed by the binding of an antisense oligomer to its complementary target, such that the heteroduplex is substantially resistant to in vivo degradation by intracellular and extracellular nucleases, such as RNAse H, which are capable of cutting double-stranded RNA/RNA or RNA/DNA complexes.

An agent is "actively taken up by mammalian cells" when the agent can enter the cell by a mechanism other than passive diffusion across the cell membrane. The agent may be transported, for example, by "active transport", referring to transport of agents across a mammalian cell membrane by e.g. an ATP-dependent transport mechanism, or by "facilitated transport", referring to transport of antisense agents across the cell membrane by a transport mechanism that requires binding of the agent to a transport protein, which then facilitates passage of the bound agent across the membrane.

The terms "modulating expression" and/or "antisense activity" refer to the ability of an antisense oligomer to either enhance or, more typically, reduce the expression of a given protein, by interfering with the expression or translation of RNA. In the case of reduced protein expression, the antisense oligomer may directly block expression of a given gene, or contribute to the accelerated breakdown of the RNA transcribed from that gene. Morpholino oligomers as described herein are believed to act via the former (steric blocking) mechanism. Preferred antisense targets for steric blocking oligomers include the ATG start codon region, splice sites, regions closely adjacent to splice sites, and 5'-untranslated region of mRNA, although other regions have been successfully targeted using morpholino oligomers.

An "effective amount" or "therapeutically effective amount" refers to an amount of antisense oligomer administered to a mammalian subject, either as a single dose or as part of a series of doses, which is effective to produce a desired therapeutic effect, typically by inhibiting translation of a selected target nucleic acid sequence.

"Treatment" of an individual (e.g. a mammal, such as a human) or a cell is any type of intervention used in an attempt to alter the natural course of the individual or cell. Treatment includes, but is not limited to, administration of a pharmaceutical composition, and may be performed either prophylactically or subsequent to the initiation of a pathologic event or contact with an etiologic agent.

As used herein, "T cells," also known as "T lymphocytes," means a subset of lymphocytes defined by their development in the thymus and by heterodimeric receptors (T cell receptors) associated with the proteins of the CD3 complex. Most T lymphocytes have α:β heterodimeric receptors, but some T cells have γ:δ receptors. T cells include several subsets, each with distinct functions: T helper cells ($T_H$ cells or CD4$^+$ T cells), cytotoxic T cells (CD8$^+$ T cells, $T_C$ cells, or CTLs), memory T cells, regulatory T cells ($T_{reg}$ cells), and natural killer T cells (NKT cells).

As used herein, an "activated T cells" is a T cell that has been signaled to proliferate and differentiate into an effector cell. Two simultaneous signals are required to activate a T cell. One signal is provided by a peptide bound to an MHC protein on the surface of an antigen presenting cell (APC). The peptide-MHC complex signals through the T cell receptor and its associated proteins. The second signal is provided by co-stimulatory molecules on the APC (e.g., CD80 and CD86), which are recognized by a co-stimulatory receptor (e.g., CD28) on the T cell surface. The combination of the two signals stimulates the T cell to proliferate and begin to differentiate into an effector cell.

As used herein, "B cells," also known as "B lymphocytes" means a subset of lymphocytes having an immunoglobulin molecule as a cell surface receptor (B cell receptor). Upon activation by an antigen (i.e., binding of the antigen to the B cell receptor), a B cell differentiates into plasma cells producing antibody of the same specificity as its initial receptor.

A. Methods

As noted above, one embodiment of the present disclosure is directed to methods for treatment of lymphocyte-related diseases or conditions, for example T-cell mediated diseases. In general, the methods comprise administering an oligomer comprising a guanidinyl, alkylguanidinyl and/or alkylaminyl moiety to a patient in need thereof. For example, in some embodiments the oligomer is a morpholino oligomer. The guanidinyl, alkylguanidinyl and/or alkylaminyl moiety may be present at any location within the oligomer, and in certain embodiments the guanidinyl, alkylguanidinyl and/or alkylaminyl moiety is bound to the intersubunit linkage of a morpholino oligomer.

In other embodiments, a method for treatment of a lymphocyte-related disease or condition is provided, the method comprising administering an effective amount of an oligomer to a patient in need thereof, wherein the oligomer comprises a backbone having a sequence of morpholino ring structures joined by intersubunit linkages, the intersubunit linkages joining a 3'-end of one morpholino ring structure to a 5'-end of an adjacent morpholino ring structure, wherein each morpholino ring structure is bound to a base-pairing moiety, such that the oligomer can bind in a sequence-specific manner to a target nucleic acid, wherein at least one of the intersubunit linkages has the following structure (I):

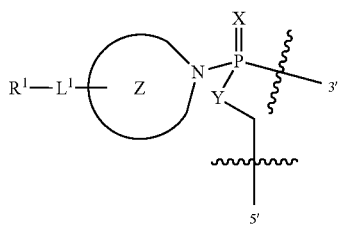

(I)

or a pharmaceutically acceptable salt, tautomer, prodrug or stereoisomer thereof, wherein:

$R^1$ is guanidinyl, alkylguanidinyl or alkylaminyl;

$L^1$ is absent or present, and when present is selected from alkylene, aminoalkylene, oxyalkylene and thioalkylene;

X is, at each occurrence, independently S or O;

Y is, at each occurrence, independently —O— or —NH—; and

Z is an optionally substituted 5, 6 or 7-membered heterocyclic ring.

In certain embodiments of the above, the lymphocyte-related disease or condition is a T-cell related disease or condition.

Various different oligomers are useful for the described methods. For example, morpholino oligomers are employed in various embodiments. In some of these embodiments, the morpholino ring structures have the following structure (i):

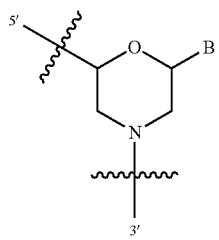

(i)

wherein B is, at each occurrence, independently a base-pairing moiety, such as A, C, G, T, I, U and the like.

In various embodiments of the above, Z is an optionally substituted 5 or 6-membered heterocyclic ring. For example, in some embodiments Z is pyrrolidinyl, or piperidinyl. In more specific embodiments, Z is piperidinyl.

In even other embodiments, Z has one of the following structures:

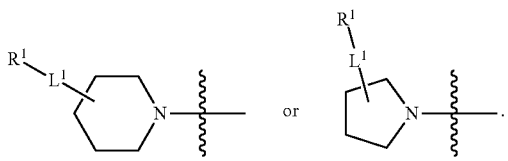

For example, in further embodiments Z has the following structure:

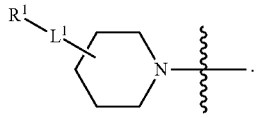

The position of the $R^1$-$L^1$ moiety on the Z ring is not particularly limited and various substitution patterns are expected to result in oligomers having the desired properties (i.e., effective delivery to lymphocytes and treatment of lymphocyte-related diseases and/or conditions). In certain embodiments, Z has the following structure:

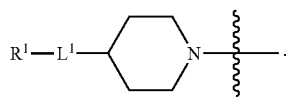

In any one of the foregoing embodiments, $R^1$ is guanidinyl.

In other of any one of the foregoing embodiments, $R^1$ is alkylguanidinyl. For example, in some embodiments the alkylguanidinyl has the following structure:

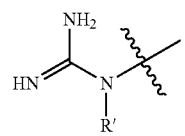

wherein R' is $C_1$-$C_6$alkyl. In further of these embodiments, R' is methyl.

In still more of any one of the foregoing embodiments, $R^1$ is alkylaminyl. For example, in certain of these embodiments the alkylaminyl is —NHR", where R" is $C_1$-$C_6$alkyl. In further of these embodiments, R" is methyl.

In some embodiments, $L^1$ is absent and $R^1$ is bound directly to the Z ring. In other embodiments, $L^1$ is selected from an appropriate length alkylene, aminoalkylene, oxyalkylene and thioalkylene such that delivery and or activity of the oligomer is optimized.

In various embodiments, X is O. In other embodiments, Y is —O—. In still other embodiments, X is O and Y is —O—.

In addition to one or more intersubunit linkages of structure (I), the oligomers typically contain additional intersubunit linkages of various structures. The structures of the other intersubunit linkages are not particularly limited, provided the oligomer comprises at least one intersubunit linkage of structure (I). In this regard, any of the intersubunit linkages known to one of ordinary skill in the art can be employed, and such intersubunit linkages will be selected to optimize the desired properties of oligomer. In some embodiments, at least one of the intersubunit linkages has the following structure (II):

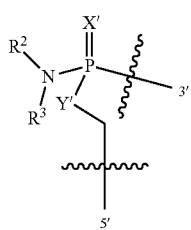

or a pharmaceutically acceptable salt, tautomer or stereoisomer thereof, wherein:

$R^2$ and $R^3$ are each independently H or $C_1$-$C_6$alkyl,

X' is S or O; and

Y' is —O— or —NH—.

In certain of the above embodiments, $R^2$ and $R^3$ are each methyl. In other embodiments, X' is O. In more embodiments, Y' is —O—.

In some of the foregoing embodiments, each intersubunit linkage in the oligomer is either linkage (I) or linkage (II). That is, certain embodiments are directed to oligomers having intersubunit linkages selected from structures (I) and (II), provided at least one intersubunit linkage has structure (I).

In some more embodiments of the above, at least one of the intersubunit linkages has the following structure:

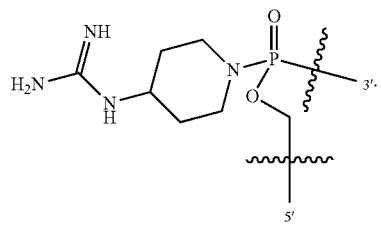 [SMILES: *COP(*)(=O)N1CCC(NC(=N)N)CC1]

In some other embodiments of the above, at least one of the intersubunit linkages has the following structure:

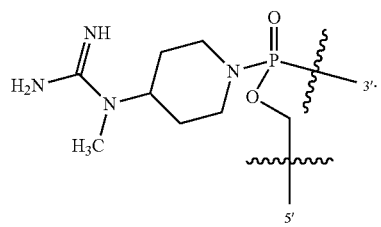 [SMILES: *COP(*)(=O)N1CCC(N(C)C(=N)N)CC1]

In even other embodiments of the above, at least one of the intersubunit linkages has the following structure:

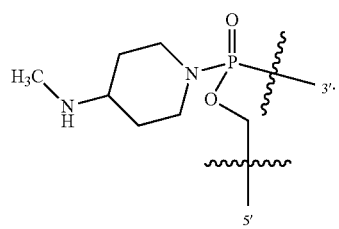 [SMILES: *COP(*)(=O)N1CCC(NC)CC1]

In certain embodiments, the lymphocyte-related disease or condition is a T-cell-related disease or condition. In some of these embodiments, the T-cell is an activated T-cell. In other embodiments, the T-cell is a CD4 or CD8 cell.

Various lymphocyte-related diseases or conditions can be treated by the disclosed methods. In various embodiments, the disease or condition is cancer or an autoimmune disease or condition.

In still other embodiments, a method for treatment of a T-cell related disease or condition is provided, the method comprising contacting activated T-cells with an oligomer comprising a backbone having a sequence of morpholino ring structures joined by intersubunit linkages, the intersubunit linkages joining a 3'-end of one morpholino ring structure to a 5'-end of an adjacent morpholino ring structure, wherein each morpholino ring structure is bound to a base-pairing moiety, such that the oligomer can bind in a sequence-specific manner to a target nucleic acid, wherein at least one of the intersubunit linkages has the following structure (I):

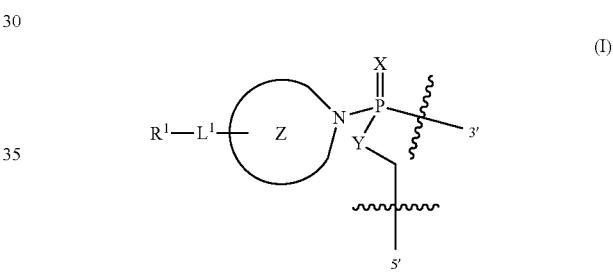

or a pharmaceutically acceptable salt, tautomer or stereoisomer thereof, wherein:

$R^1$ is guanidinyl, alkylguanidinyl or alkylaminyl;

$L^1$ is absent or present, and when present is selected from alkylene, aminoalkylene, oxyalkylene, oxoalkylene and thioalkylene;

X is, at each occurrence, independently S or O;

Y is, at each occurrence, independently —O— or —NH—; and

Z is an optionally substituted 5, 6 or 7-membered heterocyclic ring.

In various other embodiments of the foregoing, the oligomer and intersubunit linkages are as defined above.

Still other embodiments are directed to use of an oligomer comprising a backbone having a sequence of morpholino ring structures joined by intersubunit linkages, the intersubunit linkages joining a 3'-end of one morpholino ring structure to a 5'-end of an adjacent morpholino ring structure, wherein each morpholino ring structure is bound to a base-pairing moiety, such that the oligomer can bind in a sequence-specific manner to a target nucleic acid, wherein at least one of the intersubunit linkages has the following structure (I):

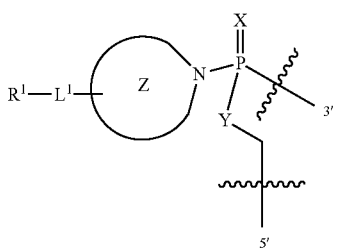

(I)

or a pharmaceutically acceptable salt, tautomer or stereoisomer thereof, wherein:

$R^1$ is guanidinyl, alkylguanidinyl or alkylaminyl;

$L^1$ is absent or present, and when present is selected from alkylene, aminoalkylene, oxyalkylene, oxoalkylene and thioalkylene;

X is, at each occurrence, independently S or O;

Y is, at each occurrence, independently —O— or —NH—; and

Z is an optionally substituted 5, 6 or 7-membered heterocyclic ring, for preparation of a pharmaceutical composition for treatment of a lymphocyte-related disease or condition.

In various other embodiments of the foregoing, the oligomer and intersubunit linkages are as defined above.

Another embodiment provides a method for improving delivery of an oligonucleotide to lymphocytes, such as T cell. The method comprises modifying the oligonucleotide to contain an intersubunit linkage having structure (I).

B. Properties of the Oligomers

As noted above, the present disclosure is directed to methods for treatment of lymphocyte-related diseases or conditions by administration of oligomers comprising various intersubunit linkage modifications, such as linkages comprising guanidinyl, alkylguanidinyl and/or alkylaminyl moieties. In certain embodiments, the oligomer comprises a backbone comprising a sequence of morpholino ring structures joined by intersubunit linkages, the intersubunit linkages joining a 3'-end of one morpholino ring structure to a 5'-end of an adjacent morpholino ring structure, wherein each morpholino ring structure is bound to a base-pairing moiety, such that the oligomer can bind in a sequence-specific manner to a target nucleic acid. The morpholino ring structures may have the following structure (i):

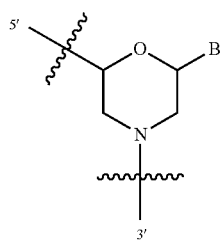

(i)

wherein B is, at each occurrence, independently a base-pairing moiety.

Each morpholino ring structure supports a base pairing moiety (B), to form a sequence of base pairing moieties which is typically designed to hybridize to a selected antisense target in a cell or in a subject being treated. The base pairing moiety may be a purine or pyrimidine found in native DNA or RNA (A, G, C, T, or U) or an analog, such as hypoxanthine (the base component of the nucleoside inosine) or 5-methyl cytosine. Analog bases that confer improved binding affinity to the oligomer can also be utilized. Exemplary analogs in this regard include C5-propynyl-modified pyrimidines, 9-(aminoethoxy)phenoxazine (G-clamp) and the like.

The oligomer may be modified, in accordance with an aspect of the invention, to include one or more linkages comprising guanidinyl, alkylguanidinyl and/or alkylaminyl moieties, e.g. up to about 1 per every 2-5 linkages, typically 3-5 per every 10 linkages. Certain embodiments also include one or more linkages comprising guanidinyl, alkylguanidinyl and/or alkylaminyl moieties.

Oligomers for use in antisense applications generally range in length from about 10 to about 40 subunits, more preferably about 15 to 25 subunits. For example, in some embodiments, an oligomer of the invention having 19-20 subunits, a useful length for an antisense oligomer, may ideally have one to seven, e.g. four to six, or three to five linkages comprising guanidinyl, alkylguanidinyl and/or alkylaminyl moieties.

The morpholino subunits may also be linked by non-phosphorus-based intersubunit linkages.

Other oligonucleotide analog linkages which are uncharged in their unmodified state but which could also bear a pendant amine substituent can also be used. For example, in certain embodiments a 5'nitrogen atom on a morpholino ring could be employed in a sulfamide linkage (or a urea linkage, where phosphorus is replaced with carbon or sulfur, respectively).

In some embodiments for antisense applications, the oligomer may be 100% complementary to the nucleic acid target sequence, or it may include mismatches, e.g., to accommodate variants, as long as a heteroduplex formed between the oligomer and nucleic acid target sequence is sufficiently stable to withstand the action of cellular nucleases and other modes of degradation which may occur in vivo. Mismatches, if present, are less destabilizing toward the end regions of the hybrid duplex than in the middle. The number of mismatches allowed will depend on the length of the oligomer, the percentage of G:C base pairs in the duplex, and the position of the mismatch(es) in the duplex, according to well understood principles of duplex stability. Although such an antisense oligomer is not necessarily 100% complementary to the nucleic acid target sequence, it is effective to stably and specifically bind to the target sequence, such that a biological activity of the nucleic acid target, e.g., expression of encoded protein(s), is modulated.

The stability of the duplex formed between an oligomer and the target sequence is a function of the binding $T_m$ and the susceptibility of the duplex to cellular enzymatic cleavage. The $T_m$ of an antisense compound with respect to complementary-sequence RNA may be measured by conventional methods, such as those described by Hames et al., Nucleic Acid Hybridization, IRL Press, 1985, pp. 107-108 or as described in Miyada C. G. and Wallace R. B., 1987, Oligonucleotide hybridization techniques, *Methods Enzymol.* Vol. 154 pp. 94-107.

In some embodiments, each antisense oligomer has a binding $T_m$, with respect to a complementary-sequence RNA, of greater than human body temperature or in other embodiments greater than 50° C. In other embodiments $T_m$'s are in the range 60-80° C. or greater. According to well known principles, the $T_m$ of an oligomer compound, with respect to a complementary-based RNA hybrid, can be increased by increasing the ratio of C:G paired bases in the duplex, and/or by increasing the length (in base pairs) of the heteroduplex. At the same time, for purposes of optimizing cellular uptake, it may be advantageous to limit the size of the oligomer. For this reason, compounds that show high $T_m$ (50° C. or greater) at a length of 20 bases or less are generally preferred over those requiring greater than 20 bases for high $T_m$ values. For some applications, longer oligomers, for example longer than 20 bases may have certain advantages. For example, in certain embodiments longer oligomers may find particular utility for use in exon skipping or splice modulation.

The targeting sequence bases may be normal DNA bases or analogues thereof, e.g., uracil and inosine that are capable of Watson-Crick base pairing to target-sequence RNA bases.

The oligomers may also incorporate guanine bases in place of adenine when the target nucleotide is a uracil residue. This is useful when the target sequence varies across different target alleles or viral species and the variation at any given nucleotide residue is either cytosine or uracil. By utilizing guanine in the targeting oligomer at the position of variability, the well-known ability of guanine to base pair with uracil (termed C/U:G base pairing) can be exploited. By incorporating guanine at these locations, a single oligomer can effectively target a wider range of RNA target variability.

The compounds (e.g., oligomers, morpholino subunits, intersubunit linkages, etc.) may exist in different isomeric forms, for example structural isomers (e.g., tautomers). With regard to stereoisomers, the compounds may have chiral centers and may occur as racemates, enantiomerically enriched mixtures, individual enantiomers, mixture or diastereomers or individual diastereomers. All such isomeric forms are included within the present invention, including mixtures thereof. The compounds may also possess axial chirality which may result in atropisomers. Furthermore, some of the crystalline forms of the compounds may exist as polymorphs, which are included in the present invention. In addition, some of the compounds may also form solvates with water or other organic solvents. Such solvates are similarly included within the scope of this invention.

The oligomers described herein may be used in methods of inhibiting production of a protein or replication of a virus. Accordingly, in one embodiment a nucleic acid encoding such a protein is exposed to an oligomer as disclosed herein. In further embodiments of the foregoing, the antisense oligomer comprises one or more intersubunit linkages comprising a guanidinyl, alkylguanidinyl and/or alkylaminyl moiety, as disclosed herein, and the base pairing moieties B form a sequence effective to hybridize to a portion of the nucleic acid at a location effective to inhibit production of the protein. In one embodiment, the location is an ATG start codon region of an mRNA, a splice site of a pre-mRNA, or a viral target sequence as described below.

In one embodiment, the oligomer has a $T_m$ with respect to binding to the target sequence of greater than about 50° C., and it is taken up by mammalian cells or bacterial cells.

The preparation and properties of morpholino oligomers is described in more detail below and in U.S. Pat. No. 5,185,444 and WO/2009/064471, each of which is hereby incorporated by reference in their entirety.

C. Formulation and Administration of the Oligomers

The present disclosure also provides for formulation and delivery of the disclosed oligomers (e.g., for treatment of lymphocyte-related diseases and/or conditions). Accordingly, in one embodiment the present disclosure is directed to a composition comprising oligomer as disclosed herein and a pharmaceutically acceptable vehicle. Other embodiments are directed to use of such a composition for treatment of a lymphocyte-related disease and/or condition.

Effective delivery of the antisense oligomer to the target nucleic acid is an important aspect of treatment. Routes of antisense oligomer delivery include, but are not limited to, various systemic routes, including oral and parenteral routes, e.g., intravenous, subcutaneous, intraperitoneal, and intramuscular, as well as inhalation, transdermal and topical delivery. The appropriate route may be determined by one of skill in the art, as appropriate to the condition of the subject under treatment. For example, the oligomer may be delivered directly to the bloodstream.

The antisense oligomer may be administered in any convenient vehicle which is physiologically and/or pharmaceutically acceptable. Such a composition may include any of a variety of standard pharmaceutically acceptable carriers employed by those of ordinary skill in the art. Examples include, but are not limited to, saline, phosphate buffered saline (PBS), water, aqueous ethanol, emulsions, such as oil/water emulsions or triglyceride emulsions, tablets and capsules. The choice of suitable physiologically acceptable carrier will vary depending upon the chosen mode of administration.

The compounds (e.g., oligomers) of the present invention may generally be utilized as the free acid or free base. Alternatively, the compounds of this invention may be used in the form of acid or base addition salts. Acid addition salts of the free amino compounds of the present invention may be prepared by methods well known in the art, and may be formed from organic and inorganic acids. Suitable organic acids include maleic, fumaric, benzoic, ascorbic, succinic, methanesulfonic, acetic, trifluoroacetic, oxalic, propionic, tartaric, salicylic, citric, gluconic, lactic, mandelic, cinnamic, aspartic, stearic, palmitic, glycolic, glutamic, and benzenesulfonic acids. Suitable inorganic acids include hydrochloric, hydrobromic, sulfuric, phosphoric, and nitric acids. Base addition salts included those salts that form with the carboxylate anion and include salts formed with organic and inorganic cations such as those chosen from the alkali and alkaline earth metals (for example, lithium, sodium, potassium, magnesium, barium and calcium), as well as the ammonium ion and substituted derivatives thereof (for example, dibenzylammonium, benzylammonium, 2-hydroxyethylammonium, and the like). Thus, the term "pharmaceutically acceptable salt" of structure (I) is intended to encompass any and all acceptable salt forms.

In addition, prodrugs are also included within the context of this invention. Prodrugs are any covalently bonded carriers that release a compound of structure (I) in vivo when such prodrug is administered to a patient. Prodrugs are generally prepared by modifying functional groups of the active moiety in a way such that the modification is cleaved, either by routine manipulation or in vivo, yielding the parent compound. Prodrugs include, for example, compounds of this invention wherein hydroxy, amine or sulfhydryl groups are bonded to any group that, when administered to a patient, cleaves to form the hydroxy, amine or sulfhydryl groups. Thus, representative examples of prodrugs include (but are not limited to) acetate, formate and benzoate derivatives of alcohol and amine functional groups of the compounds of structure (I). Further, in the case of a carboxylic acid (—COOH), esters may be employed, such as methyl esters, ethyl esters, and the like.

In some instances, liposomes may be employed to facilitate uptake of the antisense oligonucleotide into cells. (See, e.g., Williams, S. A., Leukemia 10(12):1980-1989, 1996; Lappalainen et al., Antiviral Res. 23:119, 1994; Uhlmann et al., antisense oligonucleotides: a new therapeutic principle, Chemical Reviews, Volume 90, No. 4, pages 544-584, 1990; Gregoriadis, G., Chapter 14, Liposomes, Drug Carriers in Biology and Medicine, pp. 287-341, Academic Press, 1979). Hydrogels may also be used as vehicles for antisense oligomer administration, for example, as described in WO 93/01286. Alternatively, the oligonucleotides may be administered in microspheres or microparticles. (See, e.g., Wu, G. Y. and Wu, C. H., J. Biol. Chem. 262:4429-4432, 1987). Alternatively, the use of gas-filled microbubbles complexed with the antisense oligomers can enhance delivery to target tissues, as described in U.S. Pat. No. 6,245,747. Sustained release compositions may also be used. These may include semipermeable polymeric matrices in the form of shaped articles such as films or microcapsules.

In one embodiment, antisense inhibition is effective in treating a lymphocyte-related disease or conditions, by contacting lymphocytes, such as T cells, with an antisense agent described herein. The antisense agent is administered to a mammalian subject, e.g., human or domestic animal, in a suitable pharmaceutical carrier.

In one aspect of the method, the subject is a human subject, e.g., a patient diagnosed as having a lymphocyte-related disease or condition. The condition of a patient may also dictate prophylactic administration of an antisense oligomer of the invention, e.g. in the case of a patient who (1) is immunocompromised; (2) is a burn victim; (3) has an indwelling catheter; or (4) is about to undergo or has recently undergone surgery. In one preferred embodiment, the oligomer is a phosphorodiamidate morpholino oligomer, contained in a pharmaceutically acceptable carrier, and is delivered orally. In another preferred embodiment, the oligomer is a phosphorodiamidate morpholino oligomer, contained in a pharmaceutically acceptable carrier, and is delivered intravenously (i.v.).

In another application of the method, the subject is a livestock animal, e.g., a chicken, turkey, pig, cow, horse or goat, etc, and the treatment is either prophylactic or therapeutic.

In one embodiment, the antisense compound is administered in an amount and manner effective to result in a peak blood concentration of at least 200-400 nM antisense oligomer. Typically, one or more doses of antisense oligomer are administered, generally at regular intervals, for a period of about one to two weeks. Preferred doses for oral administration are from about 1-1000 mg oligomer per 70 kg. In some cases, doses of greater than 1000 mg oligomer/patient may be necessary. For i.v. administration, preferred doses are from about 0.5 mg to 1000 mg oligomer per 70 kg. The antisense oligomer may be administered at regular intervals for a short time period, e.g., daily for two weeks or less. However, in some cases the oligomer is administered intermittently over a longer period of time. Administration may be followed by, or concurrent with, administration of an antibiotic or other therapeutic treatment. The treatment regimen may be adjusted (dose, frequency, route, etc.) as indicated, based on the results of immunoassays, other biochemical tests and physiological examination of the subject under treatment.

An effective in vivo treatment regimen using the antisense oligonucleotides of the invention may vary according to the duration, dose, frequency and route of administration, as well as the condition of the subject under treatment. Accordingly, such in vivo therapy will often require monitoring by tests appropriate to the particular type of disease or condition under treatment, and corresponding adjustments in the dose or treatment regimen, in order to achieve an optimal therapeutic outcome. Treatment may be monitored, e.g., by general indicators of disease, such as complete blood count (CBC), nucleic acid detection methods, immunodiagnostic tests, or detection of heteroduplex.

The efficacy of an in vivo administered antisense oligomer of the invention in treating lymphocyte-related diseases and/or conditions may be determined from biological samples (tissue, blood, urine etc.) taken from a subject prior to, during and subsequent to administration of the antisense oligomer. Assays of such samples include (1) monitoring the presence or absence of heteroduplex formation with target and non-target sequences, using procedures known to those skilled in the art, e.g., an electrophoretic gel mobility assay.

D. Preparation of the Oligomers

The morpholino subunits, the modified intersubunit linkages and oligomers comprising the same can be prepared as described in the examples and in U.S. Pat. Nos. 5,185,444; 7,943,762; 8,076,476; and 8,299,206 and co-pending U.S. application Ser. No. 13/118,298, which are hereby incorporated by reference in their entirety. The morpholino subunits can be prepared according to the following general Reaction Scheme I.

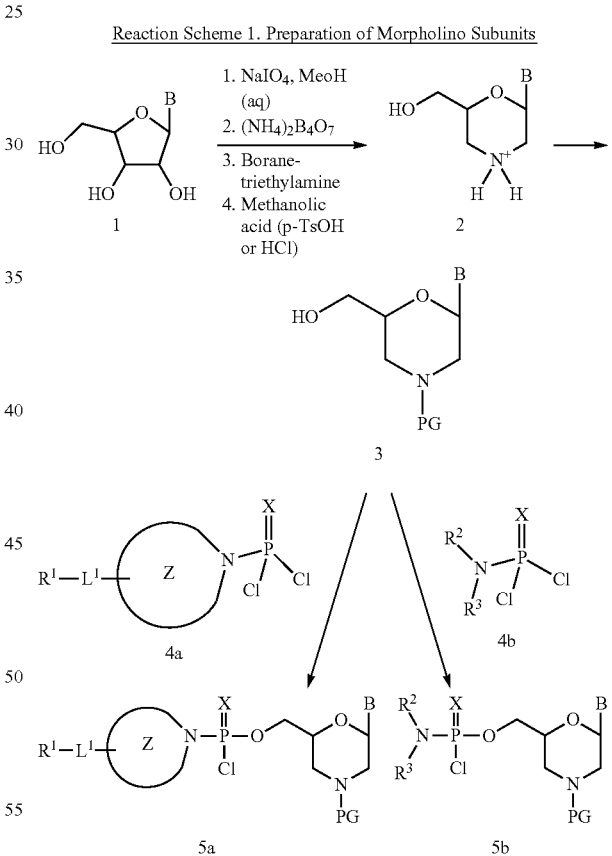

Referring to Reaction Scheme 1, wherein B represents a base pairing moiety and PG represents a protecting group, the morpholino subunits may be prepared from the corresponding ribonucleoside (1) as shown. The morpholino subunit (2) may be optionally protected by reaction with a suitable protecting group precursor, for example trityl chloride. The 3' protecting group is generally removed during solid-state oligomer synthesis as described in more detail below. The base pairing moiety may be suitably protected for solid-phase oligomer synthesis. Suitable protecting groups include benzoyl for adenine and cytosine, phenylacetyl for guanine, and pivaloyloxymethyl for hypoxanthine (I). The pivaloyloxymethyl group can be introduced onto the N1 position of the hypoxanthine heterocyclic base. Although an unprotected hypoxanthine subunit, may be employed, yields in activation reactions are far superior when the base is protected. Other suitable protecting groups include those disclosed in U.S. Pat. No. 8,076,476, which is hereby incorporated by reference in its entirety.

Reaction of 3 with the activated phosphorous compound 4a or 4b results in morpholino subunits having the desired linkage moiety (5a or 5b). It should be noted that the $R^1$ and/or $L^1$ moieties may also be installed on the heterocyclic ring Z after formation of the P—C bond or even after the subunit has been incorporated into an oligomer.

Compounds of structure 4a or 4b can be prepared using any number of methods known to those of skill in the art, including those described in the examples. Coupling with the morpholino moiety then proceeds as outlined above.

Compounds of structure 5a or 5b can be used in solid-phase automated oligomer synthesis for preparation of oligomers comprising the intersubunit linkages. Such methods are well known in the art. Briefly, a compound of structure 5a or 5b may be modified at the 5' end to contain a linker to a solid support. Once supported, the protecting group of 5a or 5b (e.g., trityl) is removed and the free amine is reacted with an activated phosphorous moiety of a second compound of structure 5 (or analogue thereof). This sequence is repeated until the desired length oligo is obtained. The protecting group in the terminal 5' end may either be removed or left on if a 5'-modification is desired. The oligo can be removed from the solid support using any number of methods, or example treatment with a base to cleave the linkage to the solid support.

The preparation of modified morpholino subunits and morpholino oligomers are described in more detail in the Examples. The morpholino oligomers containing any number of modified linkages may be prepared using methods described herein, methods known in the art and/or described by reference herein.

E. Antisense Targets of the Oligomers

The present applicants have unexpectedly discovered that the described oligomers (e.g., oligomers comprising gaunidinyl, alkylguanidinyl and/or alkylaminyl substituents on one or more intersubunit linkage) are highly effective for delivery to lymphocytes, such as T cells. Accordingly, the described methods can be employed for treatment of any number of lymphocyte related diseases and/or conditions. In this regard, one of ordinary skill in the art will recognize the various diseases and/or conditions treatable with the oligomers and the associated target (e.g., gene sequence).

In general, the oligomers comprise a sequence targeted against a gene associated with a lymphocyte related disease or condition. Typical targeting sites within such genes include, but are not limited to start codons or splice junction sites, for example an ATG start codon region of an mRNA or a splice site of a pre-mRNA. Accordingly, certain oligomers of the invention comprise or consist of base sequences which specifically hybridize to such gene targets. In some embodiments, the oligomers have at least 90% sequence homology or at least 95% sequence homology, with the targeting site. Exemplary targets are provided in Table 1. Other targets are derivable by one of ordinary skill in the art.

TABLE 1

Exemplary Antisense Targets

| Cell or Protein | Target | Function | Indication |
|---|---|---|---|
| T-Regulatory Cells | FoxP3 | T regulatory cell transcription factor | Cancer |
| | PP1 | Inhibitor of FoxP3 | Autoimmune Disease |
| | Foxo1 | Instrumental transcription factor for T regulatory cells | Cancer |
| PD-1 | PD-1 | Downregulates CD8 T cell activation | Cancer |
| | TRAF1 | Inhibitor of PD-1 expression | Autoimmune Disease |
| CTLA-4 | CTLA-4 SA2 | Induces ligand independent CTLA-4 isoform | Autoimmune Disease |
| | CTLA-4 SA3 | Induces soluble CTLA-4 isoform | Cancer |
| Th17 | IL-17RC | Combines with IL-17RA to find IL-17A and IL-17F | Autoimmune Disease |
| | IL-17RA | Combines with IL-17RA to find IL-17A and IL-17F | Autoimmune Disease |
| | RORγ | Th17 transcription factor | Autoimmune Disease |
| | IL-22 | Promotes the homestasis of epithelia and is involved in early host defense against microbial pathogens | Autoimmune Disease (Psoriasis & Brain Inflammation) |

This description is not meant to limit the invention in any way but serves to exemplify the range of human and animal disease conditions that can be addressed using oligomers comprising the modified intersubunit linkages described herein.

EXAMPLES

Unless otherwise noted, all chemicals were obtained from Sigma-Aldrich-Fluka. Benzoyl adenosine, benzoyl cytidine, and phenylacetyl guanosine were obtained from Carbosynth Limited, UK.

Synthesis of PMO and PMO containing further linkage modifications as described herein was done using methods known in the art and described in pending U.S. application Ser. Nos. 12/271,036 and 12/271,040 and PCT publication number WO/2009/064471, which are hereby incorporated by reference in their entirety.

PMO with a 3' trityl modification are synthesized essentially as described in PCT publication number WO/2009/064471 with the exception that the detritylation step is omitted.

Example 1

TERT-BUTYL 4-(2,2,2-TRIFLUOROACETAMIDO)PIPERIDINE-1-CARBOXYLATE

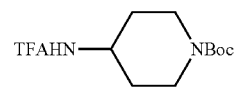

To a suspension of tert-butyl 4-aminopiperidine-1-carboxylate (48.7 g, 0.243 mol) and DIPEA (130 mL, 0.749 mol) in DCM (250 mL) was added ethyl trifluoroacetate (35.6 mL, 0.300 mol) dropwise while stirring. After 20 hours, the solution was washed with citric acid solution (200 mL×3, 10% w/v aq) and sodium bicarbonate solution (200 mL×3, conc aq), dried (MgSO$_4$), and filtered through silica (24 g). The silica was washed with DCM and the combined eluant was partially concentrated (100 mL), and used directly in the next step. APCI/MS calcd. for $C_{12}H_{19}F_3N_2O_3$ 296.1, found m/z=294.9 (M−1).

Example 2

2,2,2-TRIFLUORO-N-(PIPERIDIN-4-YL)ACETAMIDE HYDROCHLORIDE

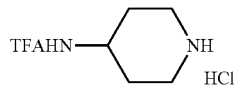

To a stirred DCM solution of the title compound of Example 1 (100 mL) was added dropwise a solution of hydrogen chloride (250 mL, 1.0 mol) in 1,4-dioxane (4 M). Stirring was continued for 6 hours, then the suspension was filtered, and the solid washed with diethyl ether (500 mL) to afford the title compound (54.2 g, 96% yield) as a white solid. APCI/MS calcd. for $C_7H_{11}F_3N_2O$ 196.1, found m/z=196.9 (M+1).

Example 3

(4-(2,2,2-TRIFLUOROACETAMIDO)PIPERIDIN-1-YL)PHOSPHONIC DICHLORIDE

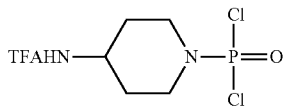

To a cooled (ice/water bath) suspension of the title compound of Example 2 (54.2 g, 0.233 mol) in DCM (250 mL) was added dropwise phosphorus oxychloride (23.9 mL, 0.256 mol) and DIPEA (121.7 mL, 0.699 mol) and stirred. After 15 minutes, the bath was removed and with continued stirring the mixture allowed to warm to ambient temperature. After 1 hour, the mixture was partially concentrated (100 mL), the suspension filtered, and the solid washed with diethyl ether to afford the title compound (43.8 g, 60% yield) as a white solid. The eluant was partially concentrated (100 mL), the resulting suspension filtered, and the solid washed with diethyl ether to afford additional title compound (6.5 g, 9% yield). ESI/MS calcd. for 1-(4-nitrophenyl)piperazine derivative $C_{17}H_{22}ClF_3N_5O_4P$ 483.1, found m/z=482.1 (M−1).

Example 4

((2S,6S)-6-((R)-5-METHYL-2,6-DIOXO-1,2,3,6-TETRAHYDROPYRIDIN-3-YL)-4-TRITYLMORPHOLIN-2-YL)METHYL (4-(2,2,2-TRIFLUOROACETAMIDO)PIPERIDIN-1-YL) PHOSPHONOCHLORIDATE

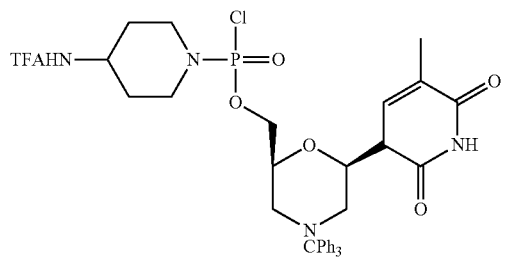

To a stirred, cooled (ice/water bath) solution of the title compound of Example 3 (29.2 g, 93.3 mmol) in DCM (100 mL) was added dropwise over 10 minutes a DCM solution (100 mL) of Mo(Tr)T # (22.6 g, 46.7 mmol), 2,6-Lutidine (21.7 mL, 187 mmol), and 4-(dimethylamino)pyridine (1.14 g, 9.33 mmol). The bath was allowed to warm to ambient temperature. After 15 hours, the solution was washed with a citric acid solution (200 mL×3, 10% w/v aq), dried (MgSO$_4$), concentrated, and the crude oil was loaded directly onto column. Chromatography [SiO$_2$ column (120 g), hexanes/EtOAc eluant (gradient 1:1 to 0:1), repeated ×3] fractions were concentrated to provide the title compound (27.2 g, 77% yield) as a white solid. ESI/MS calcd. for the 1-(4-nitrophenyl)piperazine derivative $C_{46}H_{50}F_3N_8O_8P$ 930.3, found m/z=929.5 (M−1).

Example 5

((2S,6R)-6-(6-BENZAMIDO-9H-PURIN-9-YL)-4-TRITYLMORPHOLIN-2-YL)METHYL (2,2,2-TRIFLUOROACETAMIDO)PIPERIDIN-1-YL) PHOSPHONOCHLORIDATE

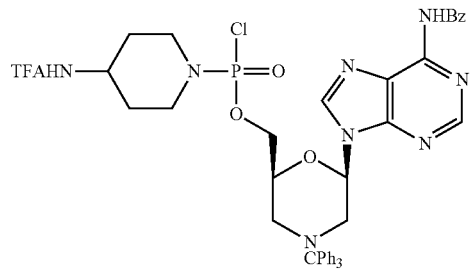

The title compound was synthesized in a manner analogous to that described in Example 4 to afford the title compound (15.4 g, 66% yield) as a white solid. ESI/MS calcd. for 1-(4-nitrophenyl)piperazine derivative $C_{53}H_{53}F_3N_{11}O_7P$ 1043.4, found m/z=1042.5 (M−1).

Example 6

Global Guanidinylation of Oligomers

An appropriate amount of an oligomer containing an aminopiperidine linkage (or methylated analogue thereof)

prepared as described above (25 mg, 2.8 µmol) was weighed into a vial (6 ml). 1H-Pyrozole-1-carboxamidine chloride (15 mg, 102 µmol) and potassium carbonate (20 mg, 0.15 mmol) were added to the vial. Water was added (500 ul), and the reaction mixture was stirred at room temperature overnight (about 18 hours). Reaction completion was determined by MALDI.

Once complete, the reaction was diluted with 1% ammonia in water (10 ml) and loaded on to an SPE column (2 cm). The vial was rinsed with 1% ammonia solution (2×2 ml), and the SPE column was washed with 1% ammonia in water (3×6 ml). Product was eluted with 45% acetonitrile in 1% ammonia in water (6 ml). Fractions containing oligomer were identified by UV optical density measurement. Product was isolated by lyophilization. Purity and identity were determined by MALDI and HPLC (C-18 and/or SAX).

Example 7

Preparation of Morpholino Oligomers

Preparation of trityl piperazine phenyl carbamate 35 (see FIG. 3): To a cooled suspension of compound 11 in dichloromethane (6 mL/g 11) was added a solution of potassium carbonate (3.2 eq) in water (4 mL/g potassium carbonate). To this two-phase mixture was slowly added a solution of phenyl chloroformate (1.03 eq) in dichloromethane (2 g/g phenyl chloroformate). The reaction mixture was warmed to 20° C. Upon reaction completion (1-2 hr), the layers were separated. The organic layer was washed with water, and dried over anhydrous potassium carbonate. The product 35 was isolated by crystallization from acetonitrile. Yield=80%

Preparation of carbamate alcohol 36: Sodium hydride (1.2 eq) was suspended in 1-methyl-2-pyrrolidinone (32 mL/g sodium hydride). To this suspension were added triethylene glycol (10.0 eq) and compound 35 (1.0 eq). The resulting slurry was heated to 95° C. Upon reaction completion (1-2 hr), the mixture was cooled to 20° C. To this mixture was added 30% dichloromethane/methyl tert-butyl ether (v:v) and water. The product-containing organic layer was washed successively with aqueous NaOH, aqueous succinic acid, and saturated aqueous sodium chloride. The product 36 was isolated by crystallization from dichloromethane/methyl tert-butyl ether/heptane. Yield=90%.

Preparation of Tail acid 37: To a solution of compound 36 in tetrahydrofuran (7 mL/g 36) was added succinic anhydride (2.0 eq) and DMAP (0.5 eq). The mixture was heated to 50° C. Upon reaction completion (5 hr), the mixture was cooled to 20° C. and adjusted to pH 8.5 with aqueous NaHCO3. Methyl tert-butyl ether was added, and the product was extracted into the aqueous layer. Dichloromethane was added, and the mixture was adjusted to pH 3 with aqueous citric acid. The product-containing organic layer was washed with a mixture of pH=3 citrate buffer and saturated aqueous sodium chloride. This dichloromethane solution of 37 was used without isolation in the preparation of compound 38.

Preparation of 38: To the solution of compound 37 was added N-hydroxy-5-norbornene-2,3-dicarboxylic acid imide (HONB) (1.02 eq), 4-dimethylaminopyridine (DMAP) (0.34 eq), and then 1-(3-dimethylaminopropyl)-N'-ethylcarbodiimide hydrochloride (EDC) (1.1 eq). The mixture was heated to 55° C. Upon reaction completion (4-5 hr), the mixture was cooled to 20° C. and washed successively with 1:1 0.2 M citric acid/brine and brine. The dichloromethane solution underwent solvent exchange to acetone and then to N,N-dimethylformamide, and the product was isolated by precipitation from acetone/N,N-dimethylformamide into saturated aqueous sodium chloride. The crude product was reslurried several times in water to remove residual N,N-dimethylformamide and salts. Yield=70% of 38 from compound 36. Introduction of the activated "Tail" onto the disulfide anchor-resin was performed in NMP by the procedure used for incorporation of the subunits during solid phase synthesis.

Preparation of the Solid Support for Synthesis of Morpholino Oligomers: This procedure was performed in a silanized, jacketed peptide vessel (custom made by Chem-Glass, N.J., USA) with a coarse porosity (40-60 µm) glass frit, overhead stirrer, and 3-way Teflon stopcock to allow N2 to bubble up through the frit or a vacuum extraction. Temperature control was achieved in the reaction vessel by a circulating water bath.

The resin treatment/wash steps in the following procedure consist of two basic operations: resin fluidization and solvent/solution extraction. For resin fluidization, the stopcock was positioned to allow N2 flow up through the frit and the specified resin treatment/wash was added to the reactor and allowed to permeate and completely wet the resin. Mixing was then started and the resin slurry mixed for the specified time. For solvent/solution extraction, mixing and N2 flow were stopped and the vacuum pump was started and then the stopcock was positioned to allow evacuation of resin treatment/wash to waste. All resin treatment/wash volumes were 15 mL/g of resin unless noted otherwise.

To aminomethylpolystyrene resin (100-200 mesh; ~1.0 mmol/g N2 substitution; 75 g, 1 eq, Polymer Labs, UK, part #1464-X799) in a silanized, jacketed peptide vessel was added 1-methyl-2-pyrrolidinone (NMP; 20 ml/g resin) and the resin was allowed to swell with mixing for 1-2 hr. Following evacuation of the swell solvent, the resin was washed with dichloromethane (2×1-2 min), 5% diisopropylethylamine in 25% isopropanol/dichloromethane (2×3-4 min) and dichloromethane (2×1-2 min). After evacuation of the final wash, the resin was fluidized with a solution of disulfide anchor 34 in 1-methyl-2-pyrrolidinone (0.17 M; 15 mL/g resin, ~2.5 eq) and the resin/reagent mixture was heated at 45° C. for 60 hr. On reaction completion, heating was discontinued and the anchor solution was evacuated and the resin washed with 1-methyl-2-pyrrolidinone (4×3-4 min) and dichloromethane (6×1-2 min). The resin was treated with a solution of 10% (v/v) diethyl dicarbonate in dichloromethane (16 mL/g; 2×5-6 min) and then washed with dichloromethane (6×1-2 min). The resin 39 (see FIG. 4) was dried under a N2 stream for 1-3 hr and then under vacuum to constant weight (±2%). Yield: 110-150% of the original resin weight.

Determination of the Loading of Aminomethylpolystyrene-disulfide resin: The loading of the resin (number of potentially available reactive sites) is determined by a spectrometric assay for the number of triphenylmethyl (trityl) groups per gram of resin.

A known weight of dried resin (25±3 mg) is transferred to a silanized 25 ml volumetric flask and ~5 mL of 2% (v/v) trifluoroacetic acid in dichloromethane is added. The contents are mixed by gentle swirling and then allowed to stand for 30 min. The volume is brought up to 25 mL with additional 2% (v/v) trifluoroacetic acid in dichloromethane and the contents thoroughly mixed. Using a positive displacement pipette, an aliquot of the trityl-containing solution (500 µL) is transferred to a 10 mL volumetric flask and the volume brought up to 10 mL with methanesulfonic acid.

The trityl cation content in the final solution is measured by UV absorbance at 431.7 nm and the resin loading calculated in trityl groups per gram resin (µmol/g) using the appropriate volumes, dilutions, extinction coefficient (ε: 41 µmol-1 cm-1) and resin weight. The assay is performed in triplicate and an average loading calculated.

The resin loading procedure in this example will provide resin with a loading of approximately 500 µmol/g. A loading of 300-400 in µmol/g was obtained if the disulfide anchor incorporation step is performed for 24 hr at room temperature.

Tail loading: Using the same setup and volumes as for the preparation of aminomethylpolystyrene-disulfide resin, the Tail can be introduced into the molecule. For the coupling step, a solution of 38 (0.2 M) in NMP containing 4-ethylmorpholine (NEM, 0.4 M) was used instead of the disulfide anchor solution. After 2 hr at 45° C., the resin 39 was washed twice with 5% diisopropylethylamine in 25% isopropanol/dichloromethane and once with DCM. To the resin was added a solution of benzoic anhydride (0.4 M) and NEM (0.4 M). After 25 min, the reactor jacket was cooled to room temperature, and the resin washed twice with 5% diisopropylethylamine in 25% isopropanol/dichloromethane and eight times with DCM. The resin 4 was filtered and dried under high vacuum. The loading for resin 40 is defined to be the loading of the original aminomethylpolystyrene-disulfide resin 39 used in the Tail loading.

Solid Phase Synthesis: Morpholino Oligomers were prepared on a Gilson AMS-422 Automated Peptide Synthesizer in 2 mL Gilson polypropylene reaction columns (Part #3980270). An aluminum block with channels for water flow was placed around the columns as they sat on the synthesizer. The AMS-422 will alternatively add reagent/wash solutions, hold for a specified time, and evacuate the columns using vacuum.

For oligomers in the range up to about 25 subunits in length, aminomethylpolystyrene-disulfide resin with loading near 500 µmol/g of resin is preferred. For larger oligomers, aminomethylpolystyrene-disulfide resin with loading of 300-400 µmol/g of resin is preferred. If a molecule with 5'-Tail is desired, resin that has been loaded with Tail is chosen with the same loading guidelines.

The following reagent solutions were prepared:
Detritylation Solution: 10% Cyanoacetic Acid (w/v) in 4:1 dichloromethane/acetonitrile; Neutralization Solution: 5% Diisopropylethylamine in 3:1 dichloromethane/isopropanol; Coupling Solution: 0.18 M (or 0.24 M for oligomers having grown longer than 20 subunits) activated Morpholino Subunit of the desired base and linkage type and 0.4 M N ethylmorpholine, in 1,3-dimethylimidazolidinone. Dichloromethane (DCM) was used as a transitional wash separating the different reagent solution washes.

On the synthesizer, with the block set to 42° C., to each column containing 30 mg of aminomethylpolystyrene-disulfide resin (or Tail resin) was added 2 mL of 1-methyl-2-pyrrolidinone and allowed to sit at room temperature for 30 min. After washing with 2 times 2 mL of dichloromethane, the following synthesis cycle was employed:

| Step | Volume | Delivery | Hold time |
|---|---|---|---|
| Detritylation | 1.5 mL | Manifold | 15 seconds |
| Detritylation | 1.5 mL | Manifold | 15 seconds |
| Detritylation | 1.5 mL | Manifold | 15 seconds |
| Detritylation | 1.5 mL | Manifold | 15 seconds |
| Detritylation | 1.5 mL | Manifold | 15 seconds |
| Detritylation | 1.5 mL | Manifold | 15 seconds |
| Detritylation | 1.5 mL | Manifold | 15 seconds |
| DCM | 1.5 mL | Manifold | 30 seconds |
| Neutralization | 1.5 mL | Manifold | 30 seconds |
| Neutralization | 1.5 mL | Manifold | 30 seconds |
| Neutralization | 1.5 mL | Manifold | 30 seconds |
| Neutralization | 1.5 mL | Manifold | 30 seconds |
| Neutralization | 1.5 mL | Manifold | 30 seconds |
| Neutralization | 1.5 mL | Manifold | 30 seconds |
| DCM | 1.5 mL | Manifold | 30 seconds |
| Coupling | 350 uL-500 uL | Syringe | 40 minutes |
| DCM | 1.5 mL | Manifold | 30 seconds |
| Neutralization | 1.5 mL | Manifold | 30 seconds |
| Neutralization | 1.5 mL | Manifold | 30 seconds |
| DCM | 1.5 mL | Manifold | 30 seconds |
| DCM | 1.5 mL | Manifold | 30 seconds |
| DCM | 1.5 mL | Manifold | 30 seconds |

The sequences of the individual oligomers were programmed into the synthesizer so that each column receives the proper coupling solution (A,C,G,T,I) in the proper sequence. When the oligomer in a column had completed incorporation of its final subunit, the column was removed from the block and a final cycle performed manually with a coupling solution comprised of 4-methoxytriphenylmethyl chloride (0.32 M in DMI) containing 0.89 M 4-ethylmorpholine.

Cleavage from the resin and removal of bases and backbone protecting groups: After methoxytritylation, the resin was washed 8 times with 2 mL 1-methyl-2-pyrrolidinone. One mL of a cleavage solution consisting of 0.1 M 1,4-dithiothreitol (DTT) and 0.73 M triethylamine in 1-methyl-2-pyrrolidinone was added, the column capped, and allowed to sit at room temperature for 30 min. After that time, the solution was drained into a 12 mL Wheaton vial. The greatly shrunken resin was washed twice with 300 µL of cleavage solution. To the solution was added 4.0 mL conc aqueous ammonia (stored at −20° C.), the vial capped tightly (with Teflon lined screw cap), and the mixture swirled to mix the solution. The vial was placed in a 45° C. oven for 16-24 hr to effect cleavage of base and backbone protecting groups.

Initial Oligomer Isolation: The vialed ammonolysis solution was removed from the oven and allowed to cool to room temperature. The solution was diluted with 20 mL of 0.28% aqueous ammonia and passed through a 2.5×10 cm column containing Macroprep HQ resin (BioRad). A salt gradient (A: 0.28% ammonia with B: 1 M sodium chloride in 0.28% ammonia; 0-100% B in 60 min) was used to elute the methoxytrityl containing peak. The combined fractions were pooled and further processed depending on the desired product.

Demethoxytritylation of Morpholino Oligomers: The pooled fractions from the Macroprep purification were treated with 1 M H3PO4 to lower the pH to 2.5. After initial mixing, the samples sat at room temperature for 4 min, at which time they are neutralized to pH 10-11 with 2.8% ammonia/water. The products were purified by solid phase extraction (SPE).

Amberchrome CG-300M (Rohm and Haas; Philadelphia, Pa.) (3 mL) is packed into 20 mL fritted columns (BioRad Econo-Pac Chromatography Columns (732-1011)) and the resin rinsed with 3 mL of the following: 0.28% NH4OH/80% acetonitrile; 0.5M NaOH/20% ethanol; water; 50 mM H3PO4/80% acetonitrile; water; 0.5 NaOH/20% ethanol; water; 0.28% NH4OH.

The solution from the demethoxytritylation was loaded onto the column and the resin rinsed three times with 3-6 mL 0.28% aqueous ammonia. A Wheaton vial (12 mL) was placed under the column and the product eluted by two washes with 2 mL of 45% acetonitrile in 0.28% aqueous ammonia. The solutions were frozen in dry ice and the vials placed in a freeze dryer to produce a fluffy white powder. The samples were dissolved in water, filtered through a 0.22 micron filter (Pall Life Sciences, Acrodisc 25 mm syringe filter, with a 0.2 micron HT Tuffryn membrane) using a syringe and the Optical Density (OD) was measured on a UV spectrophotometer to determine the OD units of oligomer present, as well as dispense sample for analysis. The solutions were then placed back in Wheaton vials for lyophilization.

Analysis of Morpholino Oligomers: MALDI-TOF mass spectrometry was used to determine the composition of fractions in purifications as well as provide evidence for identity (molecular weight) of the oligomers. Samples were run following dilution with solution of 3,5-dimethoxy-4-hydroxycinnamic acid (sinapinic acid), 3,4,5-trihydoxyacetophenone (THAP) or alpha-cyano-4-hydoxycinnamic acid (HCCA) as matrices.

Cation exchange (SCX) HPLC was performed using a Dionex ProPac SCX-10, 4×250 mm column (Dionex Corporation; Sunnyvale, Calif.) using 25 mM pH=5 sodium acetate 25% acetonitrile (Buffer A) and 25 mM pH=5 sodium acetate 25% acetonitrile 1.5 M potassium chloride (buffer B) (Gradient 10-100% B in 15 min) or 25 mM $KH_2PO_4$ 25% acetonitrile at pH=3.5 (buffer A) and 25 mM $KH_2PO_4$ 25% acetonitrile at pH=3.5 with 1.5 M potassium chloride (buffer B) (Gradient 0-35% B in 15 min). The former system was used for positively charged oligomers that do not have a peptide attached, while the latter was used for peptide conjugates.

Purification of Morpholino Oligomers by Cation Exchange Chromatography: The sample is dissolved in 20 mM sodium acetate, pH=4.5 (buffer A) and applied to a column of Source 30 cation exchange resin (GE Healthcare) and eluted with a gradient of 0.5 M sodium chloride in 20 mM sodium acetate and 40% acetonitrile, pH=4.5 (buffer B). The pooled fractions containing product are neutralized with conc aqueous ammonia and applied to an Amberchrome SPE column. The product is eluted, frozen, and lyophilized as above.

Example 8

In Vitro and In Vivo Testing of the Oligomers

A PMO (5'-GCT ATT ACC TTA ACC CAG-3'; SEQ ID NO: 1) designed to restore correct splicing in the enhanced green fluorescent protein (EGFP) gene was modified at the intersubunit linkage and/or the 5' and/or 3' end to produce modified PMOs, which were evaluated for their splice-correction activity and tissue distribution in the EGFP-654 transgenic mouse model (Sazani, Gemignani et al. 2002). In this model, the EGFP-654 gene encoding for functional EGFP is interrupted by an aberrantly-spliced mutated intron, and cellular uptake of EGFP targeted PMOs, such as SEQ ID NO: 1, can be evaluated by RT-PCR detection of the restored EGFP-654 splice product in tissues or detection of functional EGFP by fluorescence.

Sequences of the oligomers employed for the experiments described herein are presented in Table 2. The oligomers typically comprise a piperazine linker on the 5' end and either an ethylene glycol trimer (EG3) or guanidinyl terminal group linked thereto. The 3' end is either unmodified (H) or comprises a trityl, gaunidinyl or peptide moiety. An "*" indicates the presence of a modified intersubunit linkage, the structure of which is provided in Table 3. All other linkages are PMO.

TABLE 2

Oligomer Sequences

| Number | Sequence | Modifications | 3' End | 5' End |
|---|---|---|---|---|
| 0-1-0-730 | GCT ATT ACC TTA ACC CAG (SEQ ID NO 2) | None | H | EG3 |
| NG-10-0389 | GC*T AT*T ACC T*TA ACC CAG (SEQ ID NO: 3) | * = G-pip | Trityl | Guanidine |
| NG-12-0127 | GC*T A*T*T ACC T*TA ACC CAG (SEQ ID NO 4) | * = map | H | EG3 |
| NG-12-0128 | GC*T A*T*T ACC *T*TA ACC CAG (SEQ ID NO 5) | * = map | H | EG3 |
| NG-12-0153 | *G*C*T *A*T*T *A*C*C *T*T*A *A*C*C *C*A*G (SEQ ID NO: 6) | * = morph | H | EG3 |
| NG-12-0157 | GC*T A*T*T ACC T*TA ACC CAG (SEQ ID NO: 7) | * = MG-pip | C = (NH)$NH_2$ | EG3 |
| NG-12-0158 | GC*T A*T*T ACC *T*TA ACC CAG (SEQ ID NO 8) | * = MG-pip | C = (NH)$NH_2$ | EG3 |
| NG-08-0524 | GCT ATT ACC TTA ACC CAG (SEQ ID NO 9) | 3'-peptide | (RXRRBR)$_2$-XB | EG3 |
| NG-11-0153 | GCT ATT ACC TTA ACC CAG (SEQ ID NO 10) | 3'-peptide | $R_6$-G | EG3 |
| NG-10-0110 | GC*T AT*T ACC T*TA ACC CAG (SEQ ID NO: 11) | * = guanidinyl | Guanidinyl | EG3 |
| NG-10-0299 | GC*T AT*T ACC T*TA ACC CAG (SEQ ID NO: 12) | * = apn | H | EG3 |

TABLE 3

| Name | Structure |
|---|---|
| Structure of Intersubunit Linkages | |
| G-pip | [structure] |
| Map | [structure] |
| MG-pip | [structure] |
| Apn | [structure] |
| Morph | [structure] |
| PMO | [structure] |

Tissue Distribution

EGFP-654 transgenic mice (14-28 weeks old, female) were injected by tail vein I.V. with a G-pip modified oligomer (NG-10-0389) or a peptide-modified oligomer (NG-08-0524, X=aminohexanoic acid, B=beta-alanine) at doses of 2.5 mg/kg, 5 mg/kg, 10 mg/kg and 20 mg/kg (PBS vehicle). Tissues were harvested 7 days post injection and analyzed for presence of the oligomers. FIG. 1 presents the tissue distribution data for the 10 mg/kg dose. The data show that the G-pip modified oligomer has a higher affinity for T-cells relative to the peptide modified oligomer.

In Vitro Delivery to Lymphocytes

Splenocytes from an EGFP-654 reporter mouse were harvested and a cell suspension was made. Cells were CD3/CD28 stimulated in the presence of the oligomers from Table 2 for 24 h at 37° C. Cells were harvested from the plate and run through a flow cytometer for detection of EGFP and T and B cell markers. Activated and resting T cells were delineated using CD25 as the activation marker. Successful delivery to T cells is indicated by the presence of EGFP within the cell (i.e., EGFP positive cells).

Figure 2:
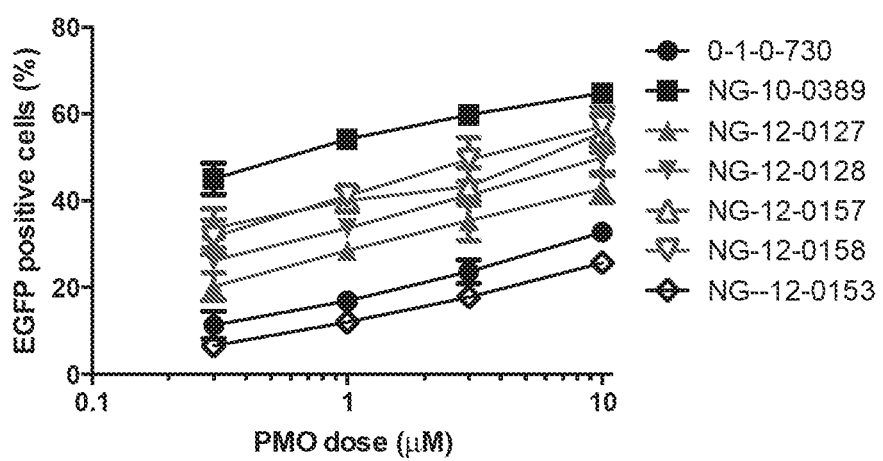
FIG. 2 is a graph showing activity of representative oligomers in activated T cells.
Figure 3:
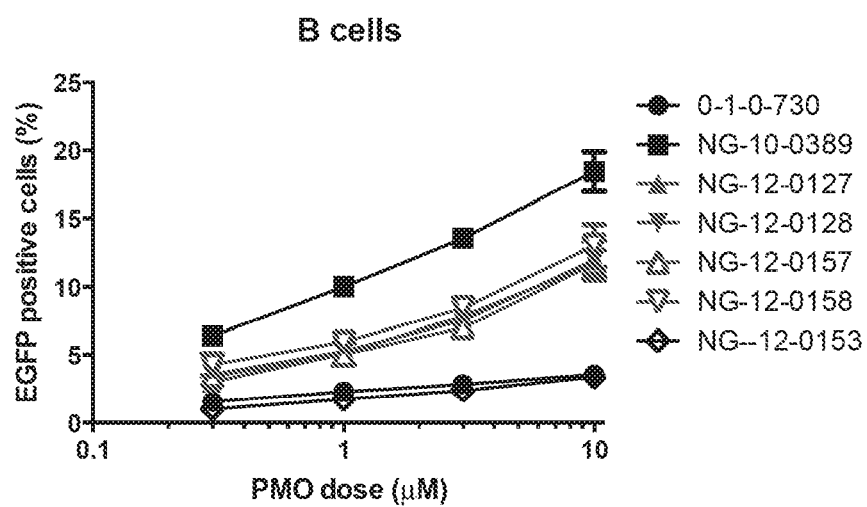
FIG. 3 presents activity data in B cells.

FIGS. 2-6 show the frequency of EGFP positive cells within each lymphocyte population for the oligomers from Table 2. FIGS. 2 and 3 present data for activated T cells and B cells, respectively. The data indicate that intersubunit linkages containing guanidinyl, alkylguanidinyl or alkylaminyl groups have higher efficacy in T cells and B cells relative to unmodified PMO (dimethylamine linkages) and morpholino PMO (morpholino linkages).

Figure 4:
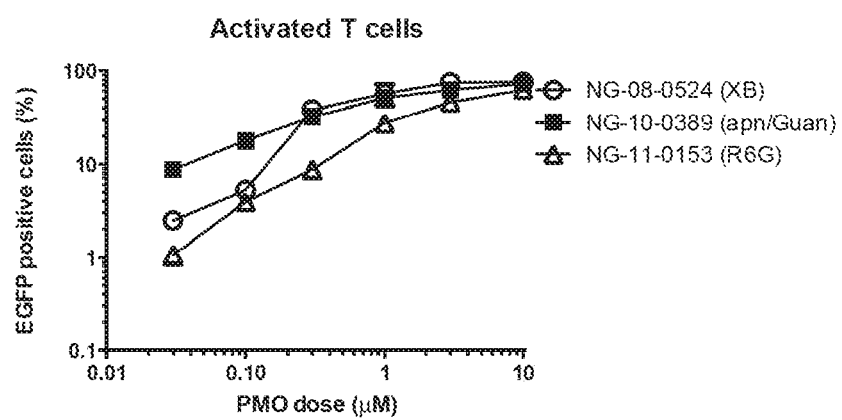
FIG. 4 compares activity of a guanidinyl modified oligomer in activated T cells relative to peptide conjugated oligomers.
Figure 5:
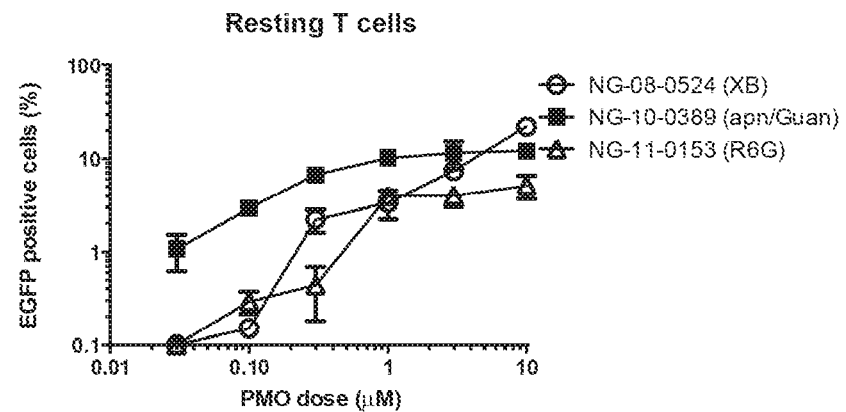
FIG. 5 illustrates comparative activity of a guanidinyl modified oligomer in resting T cells relative to peptide conjugated oligomers.
Figure 6:
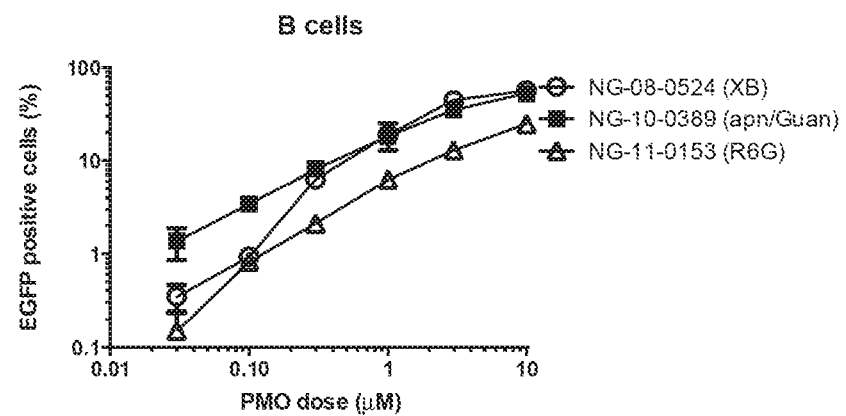
FIG. 6 presents activity of a guanidinyl modified oligomer in B cells relative to peptide conjugated oligomers.
Figure 7:
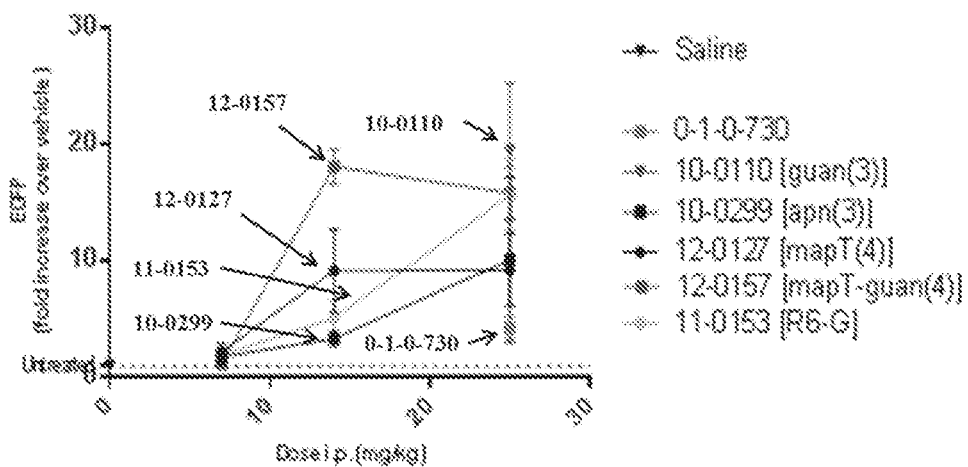
FIG. 7 is a graphical presentation of in vivo data for oligomer activities in activated T cells.
Figure 8:
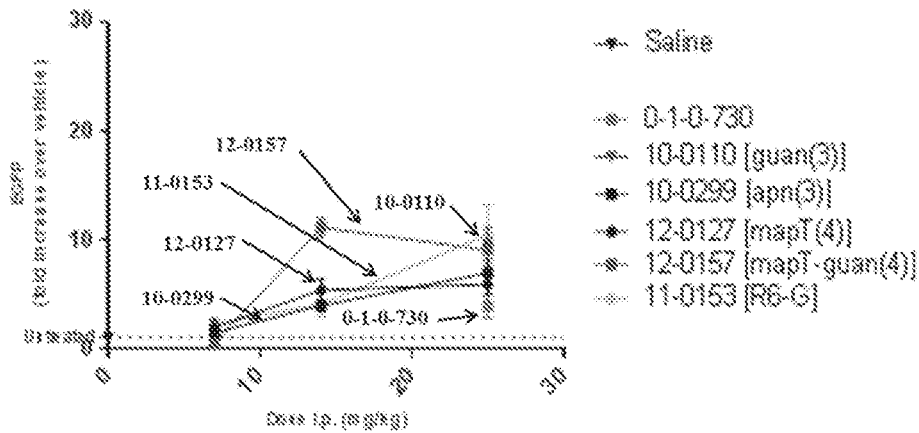
FIG. 8 shows in vivo activity data in resting T cells.
Figure 9:
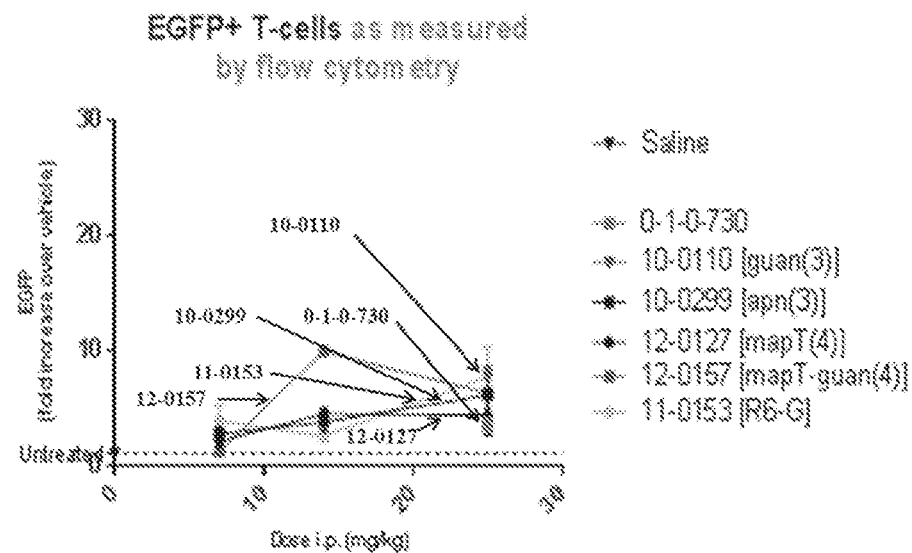
FIG. 9 presents in vivo activity of various oligomers in T cells.
Figure 10:
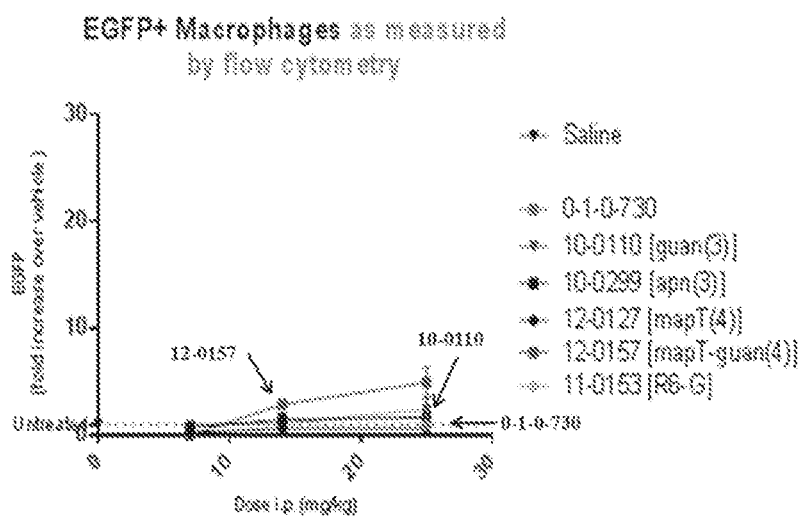
FIG. 10 provides in vivo activity of various oligomers in macrophages.

FIGS. 4, 5 and 6 present data for activated T cells, resting T cells and B cells, respectively. This data shows that oligomers having guanidinyl modifications in the intersubunit linkages having higher efficacy in T and B cells relative to peptide conjugated oligomers, especially at lower concentrations.

In Vivo Delivery to Lymphocytes

EGFP-654 reporter mice were injected with various oligomers from Table 2 as described above. Splenocytes were harvested 7 days-post injection and stained for T regulatory markers and EGFP fluorescence. The frequency of EGFP positive cells in the oligomer treated cohort was divided by the frequency of EGFP positive cells in saline treated mice to generate the fold increase in EGFP over vehicle. Results are presented in FIGS. 7-10. Again, the data indicate that intersubunit linkages containing guanidinyl, alkylguanidinyl or alkylaminyl groups have higher efficacy in T cells and macrophages relative to unmodified PMO (dimethylamine linkages) and other types of PMO modifications (e.g. peptide).

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, including but not limited to U.S. Provisional Patent Application No. 62/171,102 filed on Jun. 4, 2015, are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method for treatment of a cancer or an autoimmune disease or condition, the method comprising administering an effective amount of an oligomer to a patient in need thereof, wherein the oligomer comprises a backbone having a sequence of morpholino ring structures joined by intersubunit linkages, the intersubunit linkages joining a 3'-end of one morpholino ring structure to a 5'-end of an adjacent morpholino ring structure, wherein each morpholino ring structure is bound to a base-pairing moiety, such that the oligomer can bind in a sequence-specific manner to a target nucleic acid, wherein at least one of the intersubunit linkages has the following structure (I):

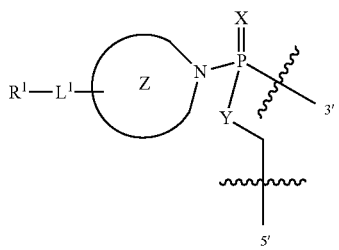
(I)

or a pharmaceutically acceptable salt, tautomer, prodrug or stereoisomer thereof, wherein:

$R^1$ is alkylaminyl;

$L^1$ is absent or present, and when present is selected from alkylene, aminoalkylene, oxyalkylene and thioalkylene;

X is, at each occurrence, independently S or O;

Y is, at each occurrence, independently —O— or —NH—; and

Z is an optionally substituted 5, 6 or 7-membered heterocyclic ring.

2. The method of claim 1, wherein the morpholino ring structures have the following structure (i):

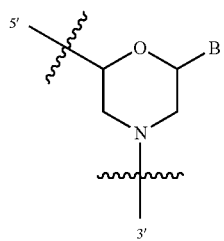
(i)

wherein B is, at each occurrence, independently a base-pairing moiety.

3. The method of claim 1, wherein Z is pyrrolidinyl.

4. The method of claim 1, wherein $R^1$-$L^1$-Z has the following structure:

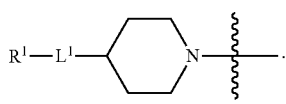

5. The method of claim 1, wherein alkylaminyl is —NHR", where R" is $C_1$-$C_6$alkyl.

6. The method of claim 1, wherein $L^1$ is absent.

7. The method of claim 1, wherein X is O.

8. The method of claim 1, wherein Y is —O—.

9. The method of claim 1, wherein at least one of the intersubunit linkages has the following structure (II):

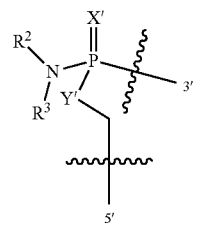
(II)

or a pharmaceutically acceptable salt, tautomer or stereoisomer thereof, wherein:

$R^2$ and $R^3$ are each independently H or $C_1$-$C_6$alkyl,

X' is S or O; and

Y' is —O— or —NH—.

10. The method of claim 1, wherein at least one of the intersubunit linkages has the following structure:

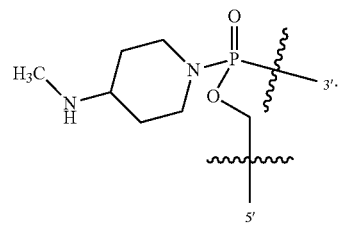 [SMILES: *COP(*)(=O)N1CCC(NC)CC1]

11. The method of claim 1, wherein the cancer or autoimmune disease or condition is a T-cell-related disease or condition.

12. The method of claim 11, wherein the T-cell is an activated T-cell, a CD4 cell, or a CD8 cell.

13. The method of claim 1, wherein the disease or condition is cancer.

14. The method of claim 1, wherein the disease or condition is an autoimmune disease or condition.

15. The method of claim 1, wherein Z is piperidinyl.

16. The method of claim 1, wherein Z is a piperidinyl ring, $L^1$ is absent, X is O, Y is —O—, and $R^1$ is alkylaminyl.

17. A method for treatment of cancer or an autoimmune disease or condition, the method comprising contacting activated T-cells with an oligomer comprising a backbone having a sequence of morpholino ring structures joined by intersubunit linkages, the intersubunit linkages joining a 3'-end of one morpholino ring structure to a 5'-end of an adjacent morpholino ring structure, wherein each morpholino ring structure is bound to a base-pairing moiety, such that the oligomer can bind in a sequence-specific manner to a target nucleic acid, wherein at least one of the intersubunit linkages has the following structure (I):

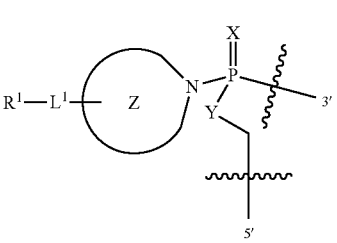
(I)

or a pharmaceutically acceptable salt, tautomer, prodrug or stereoisomer thereof, wherein:

$R^1$ is alkylaminyl;

$L^1$ is absent or present, and when present is selected from alkylene, aminoalkylene, oxyalkylene, oxoalkylene and thioalkylene;

X is, at each occurrence, independently S or O;

Y is, at each occurrence, independently —O— or —NH—; and

Z is an optionally substituted pyrrolidinyl, or piperidinyl ring.

18. The method of claim 17, wherein Z is a piperidinyl ring, $L^1$ is absent, X is O, Y is —O—, and $R^1$ is alkylaminyl.

\* \* \* \* \*